(12) United States Patent
Mihara et al.

(10) Patent No.: US 8,536,201 B2
(45) Date of Patent: Sep. 17, 2013

(54) PESTICIDAL ARYLPYRROLIDINES

(75) Inventors: Jun Mihara, Osaka (JP); Mamoru Hatazawa, Ibaraki (JP); Daiei Yamazaki, Yamaguchi (JP); Norio Sasaki, Ibaraki (JP); Tetsuya Murata, Izumi (JP); Eiichi Shimojo, Osaka (JP); Teruyuki Ichihara, Tochigi (JP); Masashi Ataka, Saitama (JP); Katsuhiko Shibuya, Tochigi (JP); Hidetoshi Kishikawa, Shiga (JP); Ulrich Görgens, Ratingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/519,819

(22) PCT Filed: Dec. 23, 2010

(86) PCT No.: PCT/EP2010/070629
§ 371 (c)(1),
(2), (4) Date: Aug. 30, 2012

(87) PCT Pub. No.: WO2011/080211
PCT Pub. Date: Jul. 7, 2011

(65) Prior Publication Data
US 2012/0322833 A1    Dec. 20, 2012

(30) Foreign Application Priority Data

Dec. 28, 2009   (JP) .................................. 2009-296889

(51) Int. Cl.
A61K 31/4439    (2006.01)
A61K 31/40      (2006.01)
A01N 43/36      (2006.01)
A01N 43/40      (2006.01)
C07D 213/44     (2006.01)
C07D 207/08     (2006.01)

(52) U.S. Cl.
USPC ......... 514/336; 546/276.4; 548/566; 514/428

(58) Field of Classification Search
USPC ............... 546/276.4; 548/566; 514/336, 428
See application file for complete search history.

(56) References Cited

U.S. PATENT DOCUMENTS 8,188,122 B2    5/2012  Mihara et al.
2010/0216792 A1  8/2010  Görgens et al.

FOREIGN PATENT DOCUMENTS

| JP | 2008-110971 A | 5/2008 |
| WO | WO 2008/122375 A2 | 10/2008 |
| WO | WO 2008/128711 A1 | 10/2008 |
| WO | WO 2010/043315 A1 | 4/2010 |
| WO | WO2010/043315 A1 * | 4/2010 |
| WO | WO 2010/124845 A1 | 11/2010 |
| WO | WO 2011/080211 A1 | 7/2011 |
| WO | WO 2012/035011 A1 | 3/2012 |

OTHER PUBLICATIONS

International Search Report dated Jan. 27, 2011 for International Application No. PCT/EP2010/070629 by the European Patent Office, Rijswijk.
Written Opinion dated Jun. 28, 2012 for International Application No. PCT/EP2010/070629 by the European Patent Office, Munich.
English language abstract for JP 2008-110971 A, espacenet database, Worldwide, published May 15, 2008.

* cited by examiner

*Primary Examiner* — Kamal Saeed
*Assistant Examiner* — Janet L Coppins
(74) *Attorney, Agent, or Firm* — Sterne, Kessler, Goldstein & Fox P.L.L.C.

(57) ABSTRACT

The present invention relates to novel pesticidal arylpyrrolidine compounds (arylpyrrolidines) having the general formula (I)

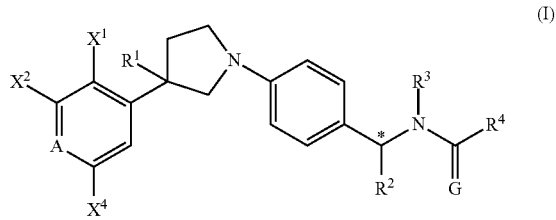

wherein A, $X^1$, $X^2$, $X^3$, $X^4$, $R^1$, $R^2$, $R^3$, $R^4$, and G are as defined in the application and their use as pesticide, in particular for combating animal pests which occur in the agricultural and/or the veterinary field, as well as to a preparation methods for preparing such compounds.

18 Claims, No Drawings

PESTICIDAL ARYLPYRROLIDINES

The present invention relates to novel pesticidal arylpyrrolidine compounds (arylpyrrolidines) and their use as pesticidal agents as well as to preparation methods for preparing such compounds.

WO 2008/128711, Japanese patent application laid-open No. 2008-110971, WO 2010/043315 and WO 2010/124845 describe that certain arylpyrrolidine compounds may be used as pesticidal agents in the agricultural field as well as in the pharmacological field.

WO 2008/128711 discloses in table 3 several arylpyrrolidine compounds having the following formula:

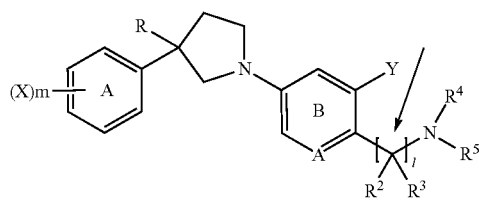

The (hetero)cyclic ring, here the ring named ring B, is with the exception of two compounds, namely compounds no. 3-1 and 3-2, always substituted by a substituent Y. Compounds 3-1 and 3-2 carry however as $R^2$ and $R^3$ just two hydrogen atoms and thus, they do not have a chiral center at the carbon atom marked with an arrow.

WO 2010/043315 discloses several arylpyrrolidine compounds having the following formulae (A-1) and (C-I), respectively:

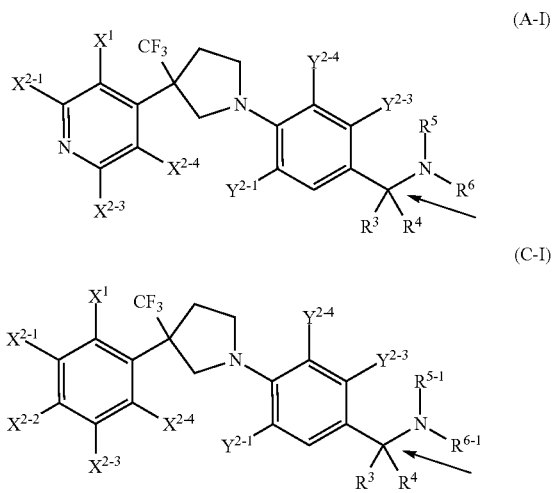

Although it is foreshadowed by WO 2010/043315 that $Y^{2-3}$ may stand for hydrogen, there are no compounds disclosed which have the formula (A-1) or (C-1) and wherein $Y^{2-3}$ is hydrogen. Additionally, among the large number of compounds disclosed in table 1 of WO 2010/043315, there are no compounds disclosed which do have a chiral center at the carbon atom marked with an arrow as in table 1 of WO 2010/043315, $R^3$ and $R^4$ are supposed to be solely hydrogen.

WO 2010/124845 discloses further pesticidal arylpyrrolidine compounds having the following structure:

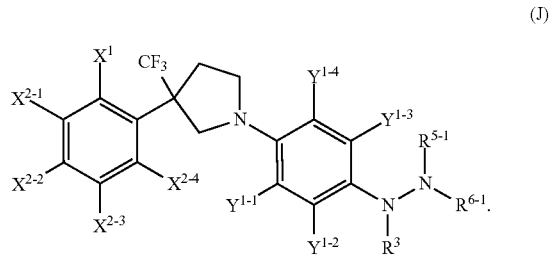

Since ecological and economic demands on modern plant treatment agents are continually increasing, particularly in respect to the amount applied, residue formation, selectivity, toxicity and biodegradability, and also because, for example, resistance problems can occur, there is the on-going task to develop new plant treatment agents that, at least in certain areas, are able to demonstrate advantages over known agents. It is particularly favorable to provide novel plant treatment agents which show a favorable degree of biodegradability so that the plant treatment agent is particularly environmentally friendly.

The inventors of the present invention conducted research to find novel arylpyrrolidine compounds which show a high degree of biological activity and having improved physico-chemical characteristics (e.g. such as biodegradability, formulation ability/stability, uptake of the active compound, onset of effect) and thus do not have all or certain of the above mentioned pitfalls. In addition, they are useful for combating (animal) pests which occur in the veterinary field (e.g. endoparasites or ectoparasites).

Thus, the invention is directed to arylpyrrolidine compounds of formula (I)

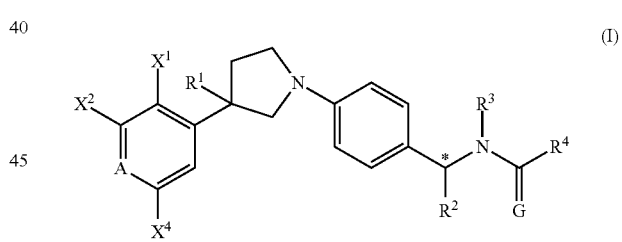

wherein
A is C—$X^3$ or nitrogen; preferably A is C—$X^3$; more preferably A is C—H, C—F, C—Cl, C—Br, C—I, or C—$CF_3$; most preferably A is C—H, C—Cl or $CCF_3$;
$X^1$, $X^2$, $X^3$ and $X^4$ are each independently hydrogen, halogen, $C_{1-4}$ haloalkyl, $C_{1-4}$ haloalkoxy, $C_{1-4}$ haloalkylthio, $C_{1-4}$ haloalkylsulfinyl and $C_{1-4}$ haloalkylsulfonyl; preferably $X^1$, $X^2$, $X^3$ and $X^4$ are each independently hydrogen, halogen, or $C_{1-4}$ haloalkyl; more preferably $X^1$, $X^2$, $X^3$ and $X^4$ are each independently hydrogen, halogen or $CF_3$;
$R^1$ is $C_{1-4}$ haloalkyl; preferably $R^1$ is trifluoromethyl;
$R^2$ is $C_{1-4}$ alkyl, $C_{1-4}$ haloalkyl, $C_{3-6}$ cycloalkyl or cyano; preferably $R^2$ is methyl, ethyl or cyclopropyl; more preferably $R^2$ is methyl;
$R^3$ is hydrogen, $C_{1-4}$ alkyl or $C_{1-4}$ haloalkyl; preferably $R^3$ is hydrogen;
$R^4$ is $C_{1-4}$ alkyl, $C_{1-4}$ haloalkyl, $C_{3-6}$ cycloalkyl, $C_{3-6}$ cycloalkyl-$C_{1-4}$ alkyl; $C_{3-6}$ halocycloalkyl, $C_{1-4}$ alkoxy, $C_{1-4}$ alkoxy-$C_{1-4}$ alkyl, $C_{1-4}$ haloalkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, $C_{1-4}$ haloalkylthio-$C_{1-4}$ alkyl, $C_{1-4}$ haloalkylsulfinyl-$C_{1-4}$ alkyl, $C_{1-4}$ haloalkylsulfonyl-$C_{1-4}$ alkyl or $C_{1-4}$ alkylamino, halogen substituted phenyl; preferably $R^4$ is methyl, ethyl, cyclopropyl, cyclopropylmethyl, 2,2,2-trifluoroethyl, 2-methoxyethyl, methylthiomethyl, methylsulfinylmethyl, methylsulfonylmethyl or 2,4,6-trifluorophenyl; more preferably $R^4$ is methyl, ethyl or cyclopropyl; and G is O or S; preferably G is O.

The nitrogen atom in the pyrrolidine skeleton of the arylpyrrolidine compounds according to the invention may be substituted with an oxygen atom, or may be substituted with $C_{1-4}$ alkyl which may be substituted with halogen, or it can form a salt.

The arylpyrrolidine compounds according to the invention have at least one asymmetric carbon, so that all compounds given herein and which are according to the invention exist in the (R)- and (S)-configuration at the carbon atom marked with the asterisk (cf. (R)-configuration in formula (I-a) and (S)-configuration in formula (I-b)).

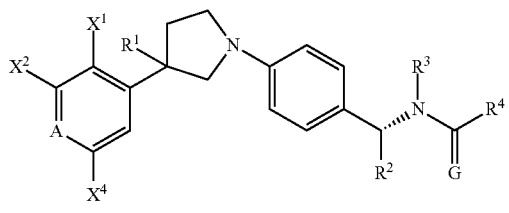

(I-a)

(R)-configuration

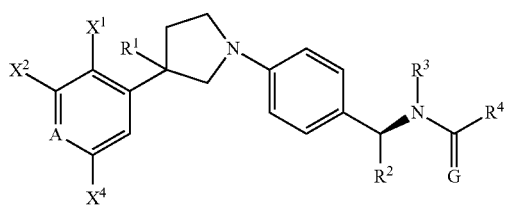

(I-b)

(S)-configuration

Although the biological activity of the racemic mixture (racemate) of the arylpyrrolidine compounds according to the invention is very high, it has been found that the (S)-configured arylpyrrolidine compounds of formula (I), i.e. compounds of formula (I-b), exhibit a much higher biological activity. In some cases, the biological activity of an isolated (S)-configured compound of formula (I-b) is up to five times higher than of the racemate. Thus, (S)-configured arylpyrrolidine compounds are preferred.

In an embodiment [A], the invention is directed to arylpyrrolidine compounds of formula (I-1) or formula (I-2), in particular in their (S)-configurations, as described for compound of formula (I-b) above,

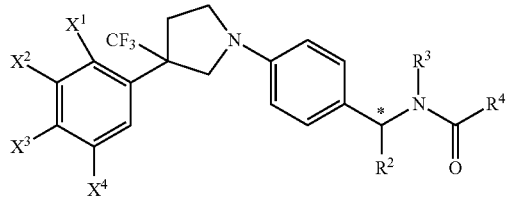

(I-1)

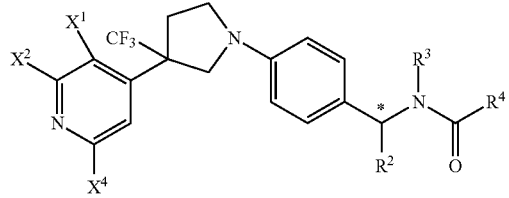

(I-2)

wherein $X^1$, $X^2$, $X^3$ and $X^4$ are each independently hydrogen, halogen or trifluoromethyl; $R^2$ is methyl, ethyl or cyclopropyl; $R^3$ is hydrogen; and $R^4$ is methyl, ethyl, cyclopropyl, cyclopropylmethyl, 2,2,2-trifluoroethyl, 2-methoxyethyl, methylthiomethyl, methylsulfinylmethyl, methylsulfonylmethyl or 2,4,6-trifluorophenyl.

In an embodiment [B], the invention is directed to arylpyrrolidine compounds of formula (I-3), in particular to compounds in their (S)-configuration, as described for compound of formula (I-b) above,

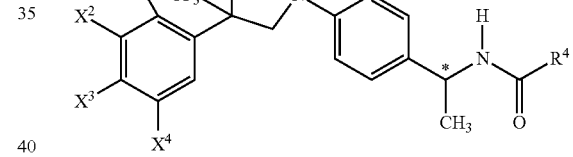

(I-3)

wherein $X^1$, $X^2$, $X^3$ and $X^4$ are each independently hydrogen, chlorine or trifluoromethyl; and $R^4$ is methyl, ethyl or cyclopropyl, cyclopropylmethyl, methoxyethyl, 2,4,6-trifluorophenyl.

In an embodiment [C], the invention is directed to arylpyrrolidine compounds of formula (I-b),

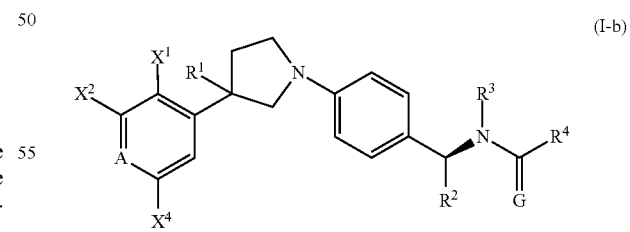

(I-b)

wherein

A is C—$X^3$ or nitrogen; $X^1$, $X^2$, $X^3$ and $X^4$ are each independently hydrogen, halogen or trifluoromethyl; $R^1$ is trifluoromethyl; $R^2$ is methyl, ethyl or cyclopropyl; $R^3$ is hydrogen; $R^4$ is methyl, ethyl, cyclopropyl, cyclopropylmethyl, 2,2,2-trifluoroethyl, 2-methoxyethyl, methylthiomethyl, methylsulfinylmethyl, methylsulfonylmethyl or 2,4,6-trifluorophenyl; and G is O.

In view of the embodiment [C], arylpyrrolidine compounds of formula (I-b) are preferred wherein A is C—$X^3$; $X^1$, $X^2$, $X^3$ and $X^4$ are each independently hydrogen, chlorine or trifluoromethyl; $R^1$ is trifluoromethyl; $R^2$ is methyl; $R^3$ is hydrogen; $R^4$ is methyl, ethyl or cyclopropyl, cyclopropylmethyl, methoxyethyl, 2,4,6-trifluorophenyl; and G is O.

In an embodiment [D], the invention is directed to arylpyrrolidine compounds of formula (I) or (I-b), wherein A is C—$X^3$; $X^1$, $X^3$, $R^3$ each is hydrogen; $X^2$, $X^4$, $R^1$ each is $CF_3$; $R^2$ is methyl; $R^4$ is methyl, ethyl or cyclopropyl, cyclopropylmethyl, methoxyethyl, 2,4,6-trifluorophenyl; and G is O.

In an embodiment [E], the invention is directed to arylpyrrolidine compounds of formula (I) or (I-b), wherein A is C—$X^3$; $X^1$, $X^3$, $R^3$ each is hydrogen; $X^2$, $X^4$ each is chlorine; $R^1$ is $CF_3$; $R^2$ is methyl; $R^4$ is methyl, ethyl or cyclopropyl; and G is O.

In an embodiment [F], the invention is directed to arylpyrrolidine compounds of formula (I) or (I-b), wherein A is C—$X^3$; $X^1$, $X^3$, $R^3$ each is hydrogen; $X^2$ is chlorine; $R^1$, $X^4$ each is $CF_3$; $R^2$ is methyl; $R^4$ is methyl, ethyl or cyclopropyl; and G is O.

In an embodiment [G], the invention is directed to arylpyrrolidine compounds of formula (I) or (I-b), wherein A is C—$X^3$; $X^1$, $R^3$ each is hydrogen; $X^2$, $X^3$, $X^4$ each is chlorine; $R^1$ is $CF_3$; $R^2$ is methyl; $R^4$ is methyl, ethyl or cyclopropyl, cyclopropylmethyl, methoxyethyl; and G is O.

In an embodiment [H], the invention is directed to arylpyrrolidine compounds of formula (I) or (I-b), wherein A is nitrogen; $X^1$, $X^3$ each is hydrogen; $X^2$, $X^4$, $R^1$ each is $CF_3$; $R^2$ is methyl; $R^4$ is cyclopropyl; and G is O.

In an embodiment [I], the invention is directed to a pesticidal composition comprising at least one arylpyrrolidine compound according to the invention for controlling insects, arachnids, helminths, nematodes, and molluscs.

In an embodiment [J], the invention is directed the pesticidal composition according to embodiment [I], which additionally comprises at least another active ingredient selected from insecticides, acaricides, nematicides, fungicides, biological control agents and bacterizides.

In an embodiment [K], the invention is directed a pharmaceutical composition comprising at least one arylpyrrolidine compound according to the invention for controlling endoparasites or ectoparasites.

The arylpyrrolidine compounds according to the invention can be prepared according to known methods and/or by the following preparation methods:

Method (a) for the preparation of arylpyrrolidine compounds according to the invention comprising reacting a compound of formula (II)

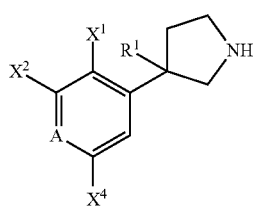

(II)

with a compound of formula (III)

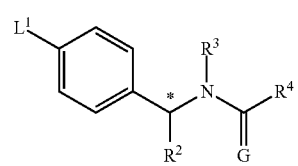

(III)

in a diluent, optionally in the presence of a base, and optionally in the presence of a catalyst wherein in the formulae (II) and (III)

A is C—$X^3$ or nitrogen; preferably A is C—$X^3$; more preferably A is C—H, C—F, C—Cl, C—Br, C—I, or C—$CF_3$; most preferably A is C—H, C—Cl or $CCF_3$;

$X^1$, $X^2$, $X^3$ and $X^4$ are each independently hydrogen, halogen, $C_{1-4}$ haloalkyl, $C_{1-4}$ haloalkoxy, $C_{1-4}$ haloalkylthio, $C_{1-4}$ haloalkylsulfinyl and $C_{1-4}$ haloalkylsulfonyl; preferably $X^1$, $X^2$, $X^3$ and $X^4$ are each independently hydrogen, halogen, or $C_{1-4}$ haloalkyl; more preferably $X^1$, $X^2$, $X^3$ and $X^4$ are each independently hydrogen, halogen or $CF_3$;

$R^1$ is $C_{1-4}$ haloalkyl; preferably $R^1$ is trifluoromethyl;

$R^2$ is $C_{1-4}$ alkyl, $C_{1-4}$ haloalkyl, $C_{3-6}$ cycloalkyl or cyano; preferably $R^2$ represents methyl, ethyl or cyclopropyl; more preferably $R^2$ is methyl;

$R^3$ is hydrogen, $C_{1-4}$ alkyl or $C_{1-4}$ haloalkyl; preferably $R^3$ is hydrogen;

$R^4$ is $C_{1-4}$ alkyl, $C_{1-4}$ haloalkyl, $C_{3-6}$ cycloalkyl, $C_{3-6}$ cycloalkyl-$C_{1-4}$ alkyl; $C_{3-6}$ halocycloalkyl, $C_{1-4}$ alkoxy, $C_{1-4}$ alkoxy-$C_{1-4}$ alkyl, $C_{1-4}$ haloalkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, $C_{1-4}$ haloalkylthio-$C_{1-4}$ alkyl, $C_{1-4}$ haloalkylsulfinyl-$C_{1-4}$ alkyl, $C_{1-4}$ haloalkylsulfonyl-$C_{1-4}$ alkyl or $C_{1-4}$ alkylamino, halogen substituted phenyl; preferably $R^4$ is methyl, ethyl, cyclopropyl, cyclopropylmethyl, 2,2,2-trifluoroethyl, 2-methoxyethyl, methylthiomethyl, methylsulfinylmethyl, methylsulfonylmethyl or 2,4,6-trifluorophenyl; more preferably $R^4$ is methyl, ethyl or cyclopropyl;

G is O or S; preferably G is O, and $L^1$ is halogen or $C_{1-4}$ haloalkylsulfonyloxy.

Compounds of formula (III) and (II) are generally known and can be prepared according to known methods.

Representative examples of the compounds of formula (III) include N-[1-(4-bromophenyl)ethyl]acetamide, N-[(1S)-1-(4-bromophenyl)ethyl]acetamide, N-[(1R)-1-(4-bromophenyl)ethyl]acetamide, N-[1-(4-bromophenyl)ethyl]propanamide, N-[(1S)-1-(4-bromophenyl)ethyl]propanamide, N-[(1R)-1-(4-bromophenyl)ethyl]propanamide, N-[1-(4-bromophenyl)ethyl]cyclopropanecarboxamide, N-[(1S)-1-(4-bromophenyl)ethyl]cyclopropanecarboxamide, N-[(1R)-1-(4-bromophenyl)ethyl]cyclopropanecarboxamide, N-[1-(4-bromophenyl)ethyl]cyclopropaneacetamide, N-[(1S)-1-(4-bromophenyl)ethyl]cyclopropaneacetamide, N-[1-(4-bromophenyl)ethyl]-3-methoxypropanamide, N-[(1S)-1-(4-bromophenyl)ethyl]-3-methoxypropanamide, N-[1-(4-bromophenyl)ethyl]-2,4,6-trifluorobenzamide and N-[(1S)-1-(4-bromophenyl)ethyl]-2,4,6-trifluorobenzamide.

Representative examples of the compounds of formula (II) include 2,6-bis(trifluoromethyl)-4-[3-(trifluoromethyl)pyrrolidin-3-yl]pyridine, 3-(3-chlorophenyl)-3-(trifluoromethyl)pyrrolidine, 3-(3-bromophenyl)-3-(trifluoromethyl)pyrrolidine, 3-(trifluoromethyl)-3-[3-(trifluoromethyl)phenyl]pyrrolidine, 3-(3,5-dichlorophenyl)-3-(trifluoromethyl)pyrrolidine, 3-(3,5-dibromophenyl)-3-(trifluoromethyl)pyrrolidine, 3-[3-chloro-5-(trifluoromethyl)phenyl]-3-(trifluoromethyl)pyrrolidine, 3-[3,5-bis(trifluoromethyl)phenyl]-3-(trifluoromethyl)pyrrolidine, 3-(3,4,5-trichlorophenyl)-3-(trifluoromethyl)pyrrolidine, 3-[3,4-dichloro-5-(trifluoromethyl)phenyl]-3-(trifluoromethyl)pyrrolidine and 2,6-bis(trifluoromethyl)-4-[3-(trifluoromethyl)pyrrolidin-3-yl]pyridine.

The compounds of formula (II) can be prepared by
(i) reacting a compound of formula (VI)

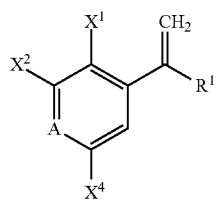

(VI)

with a substituted trimethylsilylmethyl($C_{1-6}$)alkylamine compound (e.g. N-benzyl-1-methoxy-N-[(trimethylsilyl)methyl]methanamine, N-benzyl-1-butoxy-N-[(trimethylsilyl)methyl]-methanamine or N-(butoxymethyl)-N-[(trimethylsilyl)methyl]cyclohexylamine) in the presence of a catalyst (e.g. trifluoroacetic acid, trimethylsilyl trifluoromethanesulfonate, iodotrimethylsilane or cesium fluoride) to obtain an arylpyrrolidine compound of formula (VII)

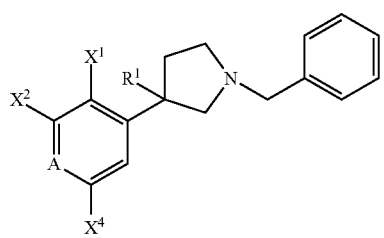

(VII)

and
(ii) removing the benzyl group (debenzylation) from the compound of formula (VII), wherein in the formulae (VI) and (VII)

A is C—$X^3$ or nitrogen; preferably A is C—$X^3$; more preferably A is C—H, C—F, C—Cl, C—Br, C—I, or C—$CF_3$; most preferably A is C—H, C—Cl or $CCF_3$;

$X^1$, $X^2$, $X^3$ and $X^4$ are each independently hydrogen, halogen, $C_{1-4}$ haloalkyl, $C_{1-4}$ haloalkoxy, $C_{1-4}$ haloalkylthio, $C_{1-4}$ haloalkylsulfinyl and $C_{1-4}$ haloalkylsulfonyl; preferably $X^1$, $X^2$, $X^3$ and $X^4$ are each independently hydrogen, halogen, or $C_{1-4}$ haloalkyl; more preferably $X^1$, $X^2$, $X^3$ and $X^4$ are each independently hydrogen, halogen or $CF_3$; and $R^1$ is $C_{1-4}$ haloalkyl; preferably $R^1$ is trifluoromethyl.

Step (i) can be carried out according to the methods described in Chemistry Letters, 1984, pp. 1117-1120 and/or Tetrahedron Letters, 1993, 34, pp. 3279-3282.

Step (ii) which is the removal of a protection group, here a benzyl group, can be carried out according to the methods described in Journal of the Organic Chemistry, 1984, 49, p. 2081, and PROTECTIVE GROUPS in ORGANIC SYNTHESIS THIRD EDITION, WILEY-INTERSCIENCE, 1999, pp. 579-580.

Compounds of formula (VI) are generally known and can be prepared according to known methods (cf. The Journal of Organic Chemistry, 1991, Vol. 56, pp. 7336-7340, ditto, 1994, Vol. 59, pp. 2898-2901, Journal of Fluorine Chemistry, 1999, vol. 95, pp. 167-170 and WO 2005/05085216).

Representative examples of the compounds of formula (VI) include 1-chloro-3-[1-(trifluoromethyl)vinyl]benzene, 1-bromo-3-[1-(trifluoromethyl)vinyl]benzene, 1-trifluoromethyl-3-[1-(trifluoromethyl)vinyl]benzene, 1,3-dichloro-5-[1-(trifluoromethyl)vinyl]benzene, 1,3-dibromo-5-[1-(trifluoromethyl)vinyl]benzene, 1-chloro-3-(trifluoromethyl)-5-[1-(trifluoromethyl)vinyl]benzene, 1,3-bis(trifluoromethyl)-5-[1-(trifluoromethyl)vinyl]benzene, 1,2,3-trichloro-5-[1-(trifluoromethyl)vinyl]benzene, 1,2-dichloro-3-trifluoromethyl-5-[1-(trifluoromethyl)vinyl]benzene and 2,6-bis(trifluoromethyl)-4-(3,3,3-trifluoroprop-1-en-2-yl)pyridine.

Preparation method (a) is carried out in a suitable diluent. Suitable diluents include for example aliphatic hydrocarbons (e.g. hexane, cyclohexane, heptane etc.), aliphatic halogenated hydrocarbons (e.g. dichloromethane, chloroform, carbon tetrachloride, dichloroethane, etc.), aromatic hydrocarbons (e.g. benzene, toluene, xylene, chlorobenzene etc.), ethers [e.g. diethyl ether, dibutyl ether, dimethoxyethane (DME), tetrahydrofuran, dioxane etc.], esters (e.g. ethyl acetate, ethyl propionate etc.), acid amides [e.g. dimethylformamide (DMF), dimethylacetamide (DMA), N-methylpyrrolidone etc.], nitriles (e.g. acetonitrile, propionitrile etc.), dimethylsulfoxide (DMSO), water or mixed solvents thereof.

It is preferred that preparation method (a) is carried out in the presence of a base. Suitable bases are alkali metal bases (e.g. lithium hydride, sodium hydride, potassium hydride, butyllithium, tert-butyllithium, trimethylsilylmethyllithium, lithium hexamethyldisilazide, sodium carbonate, potassium carbonate, cesium carbonate, tripotassium phosphate, sodium acetate, potassium acetate, sodium methoxide, sodium ethoxide, sodium tert-butoxide and potassium tert-butoxide) or organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicycloundecene, diazabicyclooctane and imidazole).

It is further preferred that the preparation method (a) is carried out in the presence of a homogeneous catalyst. Preferred catalysts are P,N-ligand stabilized transition metal complexes. Such complexes are usually formed in situ. Preferred are P-ligand stabilized palladium complexes which are formed by combining a palladium compound (e.g. $Pd_2(dba)_3$, $Pd_2(dba)_3CHCl_3$ (dba=dibenzylideneacetone), $Pd(OAc)_2$ and a phosphine ligand (e.g. "BINAP" (2,2'-bis(diphenylphosphino)-1,1'-binaphthalene), "Xantphos" (4,5-bis(diphenylphosphino)-9,9-dimethylxanthene) and tributylphosphine). Further preferred catalysts are N-ligand stabilized copper complexes which are formed by combining a copper compound (e.g. CuI, $Cu_2O$) and an amine ligand (e.g. 8-quinolinol, proline, N,N-dimethylglycine).

Preparation method (a) can be carried out within a substantially wide temperature range. It may be generally carried out at the temperature between about −78° C. and about 200° C., preferably between −10° C. and about 150° C. Said reaction is normally carried out at normal pressure although it may be carried out under elevated or reduced pressure. The reaction time is 0.1 to 72 hours, preferably 0.1 to 24 hours.

In preparation method (a) it is preferred to use the compounds of formulae (II) and (III) in an equimolar amount, or to use compound of formula (III) in an amount of 1 to 3 moles per mol of the compound of formula (II) in a suitable diluent (e.g. toluene). It is also preferred that the base (e.g. sodium tert. butoxide) is present in an amount of 1 to 3 moles per mol of the compound of formula (II), additionally to a catalytic amount of an homogeneous catalyst, such as a P,N-ligand stabilized transition metal complex (e.g. Pd$_2$(dba)$_3$CHCl$_3$ and Xantphos).

Method (b) for the preparation of arylpyrrolidine compounds according to the invention wherein R$^3$ is hydrogen comprising reacting a compound of formula (IV)

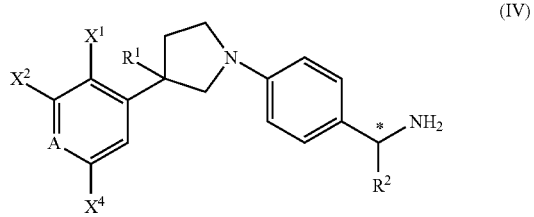
(IV)

with a compound of formula (r-1):

(r-1)

in a diluent, and optionally in the presence of a base,
wherein in the formulae (IV) and (r-1)

A is C—X$^3$ or nitrogen; preferably A is C—X$^3$; more preferably A is C—H, C—F, C—Cl, C—Br, C—I, or C—CF$_3$; most preferably A is C—H, C—Cl or CCF$_3$;

X$^1$, X$^2$, X$^3$ and X$^4$ are each independently hydrogen, halogen, C$_{1-4}$ haloalkyl, C$_{1-4}$ haloalkoxy, C$_{1-4}$ haloalkylthio, C$_{1-4}$ haloalkylsulfinyl and C$_{1-4}$ haloalkylsulfonyl; preferably X$^1$, X$^2$, X$^3$ and X$^4$ are each independently hydrogen, halogen, or C$_{1-4}$ haloalkyl; more preferably X$^1$, X$^2$, X$^3$ and X$^4$ are each independently hydrogen, halogen or CF$_3$;

R$^1$ is C$_{1-4}$ haloalkyl; preferably R$^1$ is trifluoromethyl;

R$^2$ is C$_{1-4}$ alkyl, C$_{1-4}$ haloalkyl, C$_{3-6}$ cycloalkyl or cyano; preferably R$^2$ represents methyl, ethyl or cyclopropyl; more preferably R$^2$ is methyl;

R$^4$ is C$_{1-4}$ alkyl, C$_{1-4}$ haloalkyl, C$_{3-6}$ cycloalkyl, C$_{3-6}$ cycloalkyl-C$_{1-4}$ alkyl; C$_{3-6}$ halocycloalkyl, C$_{1-4}$ alkoxy, C$_{1-4}$ alkoxy-C$_{1-4}$ alkyl, C$_{1-4}$ haloalkoxy-C$_{1-4}$ alkyl, C$_{1-4}$ alkylthio-C$_{1-4}$ alkyl, C$_{1-4}$ alkylsulfinyl-C$_{1-4}$ alkyl, C$_{1-4}$ alkylsulfonyl-C$_{1-4}$ alkyl, C$_{1-4}$ haloalkylthio-C$_{1-4}$ alkyl, C$_{1-4}$ haloalkylsulfinyl-C$_{1-4}$ alkyl, C$_{1-4}$ haloalkylsulfonyl-C$_{1-4}$ alkyl or C$_{1-4}$ alkylamino, halogen substituted phenyl; preferably R$^4$ is methyl, ethyl, cyclopropyl, cyclopropyl-methyl, 2,2,2-trifluoroethyl, 2-methoxyethyl, methylthiomethyl, methylsulfinylmethyl, methylsulfonylmethyl or 2,4,6-trifluorophenyl; more preferably R$^4$ is methyl, ethyl or cyclopropyl;

G is O or S; preferably G is O, and

L$^2$ is hydroxy, fluorine, chlorine, bromine, C$_{1-4}$ alkyl-carbonyloxy, C$_{1-4}$ alkoxy-carbonyloxy, C$_{1-4}$ alkyl-sulfonyloxy, C$_{1-4}$ haloalkyl-sulfonyloxy, arylsulfonyloxy or azolyl.

Compounds of formula (IV) are prepared according to the preparation method (a), while the reaction of compounds of formula (IV) with a compound of formula (r-1) is carried out according to standard methods known in the organic chemistry (cf. WO 2008/128711, WO 2010/043315).

Compounds of formula (r-1) are known. Representative compounds include acetic acid, propionic acid, cyclopropanecarboxylic acid, cyclopropylacetic acid, 3,3,3-Trifluoropropionic acid, 3-methoxypropionic acid, (methylthio)acetic acid, (methylsulfinyl)acetic acid, methanesulfonylacetic acid, acetyl chloride, propionyl chloride, cyclopropylcarbonyl chloride, 2,4,6-trifluorobenzoyl chloride, acetic anhydride, propionic anhydride.

The term "controlling" as used herein with regard to the agrochemical field, means that the active compounds are effective in reducing the incidence of the respective animal pest in the agriculture. More specifically, "controlling", as used herein, means that the active compound is effective in killing the respective animal pests, inhibiting its growth, or inhibiting its proliferation.

If not defined otherwise, the term "alkyl" stands for linear or branched C$_{1-4}$ alkyl, for example, methyl, ethyl, n- or iso-propyl, n-, iso-, sec- or tert-butyl. In addition, for an alkyl moiety that is comprised in other groups as a part of their constitution, the definition for the term "alkyl" applies.

If not defined otherwise, the term "haloalkyl" or the term "alkyl substituted with halogen" stands for linear or branched C$_{1-4}$ alkyl which is substituted with at least one halogen, such as for example, CH$_2$F, CHF$_2$, CF$_3$, CF$_2$Cl, CFCl$_2$, CF$_2$Br, CF$_2$CF$_3$, CFHCF$_3$, CH$_2$CF$_3$, CFClCF$_3$, CCl$_2$CF$_3$, CF$_2$CH$_3$, CF$_2$CH$_2$F, CF$_2$CHF$_2$, CF$_2$CF$_2$Cl, CF$_2$CF$_2$Br, CFHCH$_3$, CFHCHF$_2$, CFHCHF$_2$, CHFCF$_3$, CHFCF$_2$Cl, CHFCF$_2$Br, CFClCF$_3$, CCl$_2$CF$_3$, CF$_2$CF$_2$CF$_3$, CH$_2$CF$_2$CF$_3$, CF$_2$CH$_2$CF$_3$, CF$_2$CF$_2$CH$_3$, CHFCF$_2$CF$_3$, CF$_2$CHFCF$_3$, CF$_2$CF$_2$CHF$_2$, CF$_2$CF$_2$CH$_2$F, CF$_2$CF$_2$CF$_2$Cl, CF$_2$CF$_2$CF$_2$Br, CH(CHF$_2$)CF$_3$, CH(CF$_3$)CF$_3$, CF(CF$_3$)CF$_3$, CF(CF$_3$)CF$_2$Br, CF$_2$CF$_2$CF$_2$CF$_3$, CH(CF$_3$)CF$_2$CF$_3$ and CF(CF$_3$)CF$_2$CF$_3$, or perfluoroalkyl in which all substitutable hydrogen atoms of the alkyl are replaced by fluorine.

If not defined otherwise, the term "alkoxy" stands for linear or branched C$_{1-4}$ alkoxy (e.g. methoxy, ethoxy, n-propoxy, i-propoxy, n-, iso-, sec- and tert-butoxy) The alkoxy may be substituted with halogen or an optional substituent.

If not defined otherwise, the term "halogen" stands for fluorine, chlorine, bromine or iodine, preferably fluorine, chlorine or bromine.

If not defined otherwise, the term "cycloalkyl" stands for C$_{3-6}$ cycloalkyl, for example, cyclopropyl, cyclobutyl, cyclopentyl and cyclohexyl. Further, for a cycloalkyl moiety that is comprised in the other groups as a part of their constitution, those described in the above for the "cycloalkyl" can be also exemplified. Cycloalkyl substituted with halogen means halocycloalkyl, and examples thereof include fluorocyclopropyl, chlorocyclopropyl, difluorocyclopropyl, dichlorocyclopropyl, and undecafluorocyclohexyl.

The compounds according to the invention exhibit a very potent pesticidal activity. Thus, the compounds according to the invention can be used as pesticides in the agricultural field or in the veterinary field. The active compounds according to the invention may be used in combination with suitable synergists or other active compounds, such as for example insecticides, acaricides, nematicides, fungicides, biological control agents, and bacterizides. Such combinations can also result in a synergistic effect, i.e. the biological activity of such a combination is synergistically increased. Examples of such combination partners are the following insecticides, acaricides, nematicides which are sorted by their mode of action:

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, and xylylcarb; or organophosphates, e.g. acephate, azamethiphos, azinphos (-methyl, -ethyl), cadusafos, chlorethoxyfos, chlorfenvinphos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon, and vamidothion.

(2) GABA-gated chloride channel antagonists, for example organochlorines, e.g. chlordane, endosulfan (alpha-); or fiproles (phenylpyrazoles), e.g. ethiprole, fipronil, pyrafluprole, and pyriprole.

(3) Sodium channel modulators/voltage-dependent sodium channel blockers, for example pyrethroids, e.g. acrinathrin, allethrin (d-cis-trans, d-trans), bifenthrin, bioallethrin, bioallethrin S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers), esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer), prallethrin, profluthrin, pyrethrin (pyrethrum), resmethrin, RU 15525, silafluofen, tefluthrin, tetramethrin [(1R)-isomers)], tralomethrin, transfluthrin and ZXI 8901; or DDT; or methoxychlor.

(4) Nicotinergic acetylcholine receptor agonists, for example chloronicotinyls, e.g. acetamiprid, clothianidin, dinotefuran, imidacloprid, nitenpyram, thiacloprid, thiamethoxam; or nicotine.

(5) Allosteric acetylcholine receptor modulators (agonists), for example spinosyns, e.g. spinetoram and spinosad.

(6) Chloride channel activators, for example avermectins/milbemycins, e.g. abamectin, emamectin benzoate, lepimectin, and milbemectin.

(7) Juvenile hormone mimics, e.g. hydroprene, kinoprene, methoprene; or fenoxycarb; pyriproxyfen.

(8) Miscellaneous non-specific (multi-site) inhibitors, for example gassing agents, e.g. methyl bromide and other alkyl halides; or chloropicrin; sulfuryl fluoride; borax; tartar emetic.

(9) Selective homopteran feeding blockers, e.g. pymetrozine or flonicamid.

(10) Mite growth inhibitors, e.g. clofentezine, diflovidazin, hexythiazox, etoxazole.

(11) Microbial disruptors of insect midgut membranes, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis*, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example diafenthiuron; or organotin miticides, e.g. azocyclotin, cyhexatin, and fenbutatin oxide; or propargite; tetradifon.

(13) Uncouplers of oxidative phosphorylation via disruption of the proton gradient, for example chlorfenapyr, and DNOC.

(14) Nicotinic acetylcholine receptor channel blockers, for example bensultap, cartap hydrochloride, thiocyclam, and thiosultap-sodium.

(15) Inhibitors of chitin biosynthesis, type 0, for example benzoylureas, e.g. bistrifluron, chlorfluazuron, diflubenzuron, flucycloxuron, flufenoxuron, hexaflumuron, lufenuron, novaluron, noviflumuron, penfluron, teflubenzuron, and triflumuron.

(16) Inhibitors of chitin biosynthesis, type 1, for example buprofezin.

(17) Moulting disruptors, for example cyromazine.

(18) Ecdysone receptor agonists/disruptors, for example diacylhydrazines, e.g. chromafenozide, halofenozide, methoxyfenozide, and tebufenozide.

(19) Octopamine receptor agonists, for example amitraz.

(20) Mitochondrial complex III electron transport inhibitors, for example hydramethylnon; acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad, tolfenpyrad or rotenone. (Derris).

(22) Voltage-dependent sodium channel blockers, e.g. indoxacarb; metaflumizone.

(23) Inhibitors of acetyl CoA carboxylase, for example tetronic acid derivatives, e.g. spirodiclofen and spiromesifen; or tetramic acid derivatives, e.g. spirotetramat.

(24) Mitochondrial complex IV electron inhibitors, for example phosphines, e.g. aluminum phosphide, calcium phosphide, phosphine, and zinc phosphide or cyanide.

(25) Mitochondrial complex II electron transport inhibitors, for example cyenopyrafen.

(28) Ryanodine receptor modulators, for example diamides, e.g. chlorantraniliprole (Rynaxypyr), Cyantraniliprole (Cyazypyr), and flubendiamide.

Further active ingredients with unknown or uncertain mode of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulfonyl]-1,3-thiazole), flufenerim, pyridalyl, and pyrifluquinazon; furthermore products based on *Bacillus firmus* (I-1582, BioNeem, Votivo) or one of the following known active compounds:

4-{[(6-brompyrid-3-yl)methyl](2-fluorethyl)amino}furan-2 (5H)-on (known from WO 2007/115644), 4-{[(6-fluorpyrid-3-yl)methyl](2,2-difluorethyl)amino}furan-2(5H)-on (known from WO 2007/115644), 4-{[(2-chlor-1,3-thiazol-5-yl)methyl](2-fluorethyl)amino}furan-2(5H)-on (known from WO 2007/115644), 4-{[(6-chlorpyrid-3-yl)methyl](2-fluorethyl)amino}furan-2(5H)-on (known from WO 2007/115644), 4-{[(6-chlorpyrid-3-yl)methyl](2,2-difluorethyl) amino}furan-2(5H)-on known from WO 2007/115644), 4-{[(6-chlor-5-fluorpyrid-3-yl)methyl](methyl) amino}furan-2(5H)-on (known from WO 2007/115643), 4-{[(5,6-dichlorpyrid-3-yl)methyl](2-fluorethyl) amino}furan-2(5H)-on (known from WO 2007/115646), 4-{[(6-chlor-5-fluorpyrid-3-yl)methyl](cyclopropyl) amino}furan-2(5H)-on (known from WO 2007/115643), 4-{[(6-chlorpyrid-3-yl)methyl](cyclopropyl)amino}furan-2 (5H)-on (known from EP-A-0 539 588), 4-{[(6-chlorpyrid-3-yl)methyl](methyl)amino}furan-2(5H)-on (known from EP-A-0 539 588), [(6-chlorpyridin-3-yl)methyl](methyl) oxido-λ4-sulfanylidencyanamid (known from WO 2007/149134), [1-(6-chlorpyridin-3-yl)ethyl](methyl)oxido-λ4-sulfanylidencyanamid (known from WO 2007/149134) and its diastereomeres (A) and (B)

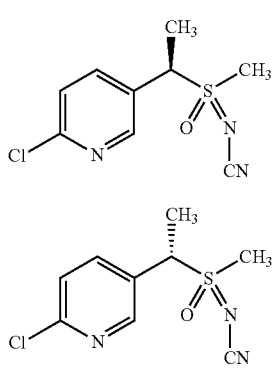

(also known from WO 2007/149134), [(6-trifluormethylpyridin-3-yl)methyl](methyl)oxido-λ4-sulfanylidencyanamid (known from WO 2007/095229), or sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911), and 1-[2-fluoro-4-methyl-5-[(2,2,2-trifluoroethyl)sulfinyl]phenyl]-3-(trifluoromethyl)-1H-1,2,4-Triazol-5-amine (known from WO 2006/043635). Examples of further combination partners are the following fungicides:

(1) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propoxy]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]1H-imidazole-1-carbothioate.

(2) Inhibitors of the respiratory chain at complex I or II, for example bixafen, boscalid, carboxin, diflumetorim, fenfuram, fluopyram, flutolanil, fluxapyroxad, furametpyr, furmecyclox, isopyrazam (mixture of syn-epimeric racemate 1RS,4SR,9RS and anti-epimeric racemate 1RS,4SR,9SR), isopyrazam (anti-epimeric racemate 1RS,4SR,9SR), isopyrazam (anti-epimeric enantiomer 1R,4S,9S), isopyrazam (anti-epimeric enantiomer 1S,4R,9R), isopyrazam (syn epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamide, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, N-[1-(2,4-dichlorophenyl)-1-methoxypropan-2-yl]-3-(difluoromethyl)-1-methyl-1H-pyrazole-4-carboxamide and salts thereof.

(3) Inhibitors of the respiratory chain at complex III, for example ametoctradin, amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, methyl (2E)-2-{2-[({cyclopropyl[(4-methoxyphenyl)imino]methyl}sulfanyl)methyl]phenyl}-3-methoxyprop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide, (2R)-2-{2-[(2,5-dimethylphenoxy)methyl]phenyl}-2-methoxy-N-methylacetamide and salts thereof.

(4) Inhibitors of the mitosis and cell division, for example benomyl, carbendazim, chlorfenazole, diethofencarb, ethaboxam, fluopicolide, fuberidazole, pencycuron, thiabendazole, thiophanate-methyl, thiophanate, zoxamide, 5-chloro-7-(4-methylpiperidin-1-yl)-6-(2,4,6-trifluorophenyl)-[1,2,4]triazolo[1,5-a]pyrimidine, 3-chloro-5-(6-chloropyridin-3-yl)-6-methyl-4-(2,4,6-trifluorophenyl)pyridazine and salts thereof.

(5) Compounds capable to have a multisite action, like for example bordeaux mixture, captafol, captan, chlorothalonil, copper hydroxide, copper naphthenate, copper oxide, copper oxychloride, copper(2+) sulfate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb, ziram and salts thereof.

(6) Compounds capable to induce a host defence, like for example acibenzolar-S-methyl, isotianil, probenazole, tiadinil and salts thereof.

(7) Inhibitors of the amino acid and/or protein biosynthesis, for example andoprim, blasticidin-S, cyprodinil, kasugamycin, kasugamycin hydrochloride hydrate, mepanipyrim, pyrimethanil and salts thereof.

(8) Inhibitors of the ATP production, for example fentin acetate, fentin chloride, fentin hydroxide and silthiofam.

(9) Inhibitors of the cell wall synthesis, for example benthiavalicarb, dimethomorph, flumorph, iprovalicarb, mandipropamid, polyoxins, polyoxorim, validamycin A and valifenalate.

(10) Inhibitors of the lipid and membrane synthesis, for example biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Inhibitors of the melanine biosynthesis, for example carpropamid, diclocymet, fenoxanil, phthalide, pyroquilon and tricyclazole.

(12) Inhibitors of the nucleic acid synthesis, for example benalaxyl, benalaxyl-M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Inhibitors of the signal transduction, for example chlozolinate, fenpiclonil, fludioxonil, iprodione, procymidone, quinoxyfen and vinclozolin.

(14) Compounds capable to act as an uncoupler, like for example binapacryl, dinocap, ferimzone, fluazinam and meptyldinocap.

(15) Further compounds, like for example benthiazole, bethoxazin, capsimycin, carvone, chinomethionat, chlazafenone, cufraneb, cyflufenamid, cymoxanil, cyprosulfamide, dazomet, debacarb, dichlorophen, diclomezine, difenzoquat, difenzoquat methylsulphate, diphenylamine, ecomate, fenpyrazamine, flumetover, fluoroimide, flusulfamide, flutianil, fosetyl-aluminum, fosetyl-calcium, fosetyl-sodium, hexachlorobenzene, irumamycin, methasulfocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and salts, phenothrin, phosphorus acid and its salts, propamocarb-fosetylate, propanosine-sodium, proquinazid, pyrrolnitrine, tebufloquin, tecloftalam, tolnifanide, triazoxide, trichlamide, zarilamid, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulfonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and salts, 3,4,5-trichloropyridine-2,6-dicarbonitrile, 3-[5-(4-chlorophenyl)-2,3-dimethyl-1,2-oxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chloro-N'-phenyl-N'-(prop-2-yn-1-yl)thiophene-2-sulfonohydrazide, 5-methyl-6-octyl[1,2,4]triazolo[1,5-a]pyrimidin-7-amine, ethyl (2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difluoromethoxy)-2,3-difluorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl{6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulfate (2:1).

(16) Further compounds like for example 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulfonyl)valinamide.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

The compounds according to the invention, in combination with good plant tolerance and favorable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development. The abovementioned animal pests include:

Order: Arthropoda: From the class of the Arachnida, for example *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Centruroides* spp., *Chorioptes* spp., *Dermanyssus gallinae*, *Dennatophagoides pteronyssius*, *Dermatophagoides farinae*, *Dermacentor* spp., *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vaejovis* spp., *Vasates lycopersici*.

From the order of the Anoplura (Phthiraptera), for example, *Damalinia* spp., *Haematopinus* spp., *Linognathus* spp., *Pediculus* spp., *Ptirus pubis*, *Trichodectes* spp.

From the order of Blattodea, for example, *Blatella germanica*, *Periplaneta americana*, *Reticulitermes speratus*, *Coptotermes formosanus*.

From the order of the Chilopoda, for example, *Geophilus* spp., *Scutigera* spp.

From the order of the Coleoptera, for example, *Acalymma vittatum*, *Acanthoscelides obtectus*, *Adoretus* spp., *Agelastica alni*, *Agriotes* spp., *Alphitobius diaperinus*, *Amphimallon solstitialis*, *Anobium punctatum*, *Anoplophora* spp., *Anthonomus* spp., *Anthrenus* spp., *Apion* spp., *Apogonia* spp., *Atomaria* spp., *Attagenus* spp., *Bruchidius obtectus*, *Bruchus* spp., *Cassida* spp., *Cerotoma trifurcata*, *Ceutorrhynchus* spp., *Chaetocnema* spp., *Cleonus mendicus*, *Conoderus* spp., *Cosmopolites* spp., *Costelytra zealandica*, *Ctenicera* spp., *Curculio* spp., *Cryptorhynchus lapathi*, *Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides*, *Hellula undalis*, *Heteronychus arator*, *Heteronyx* spp., *Hylamorpha elegans*, *Hylotrupes bajulus*, *Hypera postica*, *Hypothenemus* spp., *Lachnosterna consanguinea*, *Lema* spp., *Leptinotarsa decemlineata*, *Leucoptera* spp., *Lissorhoptrus oryzophilus*, *Lixus* spp., *Luperodes* spp., *Lyctus* spp., *Megascelis* spp., *Melanotus* spp., *Meligethes aeneus*, *Melolontha* spp., *Migdolus* spp., *Monochamus* spp., *Naupactus xanthographus*, *Niptus hololeucus*, *Oryctes rhinoceros*, *Oryzaephilus surinamensis*, *Oryzaphagus oryzae*, *Otiorrhynchus* spp., *Oxycetonia jucunda*, *Phaedon cochleariae*, *Phyllophaga* spp., *Phyllotreta* spp., *Popillia japonica*, *Premnotrypes* spp., *Prostephanus truncatus*, *Psylliodes* spp., *Ptinus* spp., *Rhizobius ventralis*, *Rhizopertha dominica*, *Sitophilus* spp., *Sphenophorus* spp., *Stegobium paniceum*, *Sternechus* spp., *Symphyletes* spp., *Tanymecus* spp., *Tenebrio molitor*, *Tribolium* spp., *Trogoderma* spp., *Tychius* spp., *Xylotrechus* spp., *Zabrus* spp. Additionally, *Callosobruchus Chinensis*, *Sitophilus zeamais*, *Tribolium castaneum*, *Epilachna vigintioctomaculata*, *Agriotes ogurae fuscicollis*, *Anomala rufocuprea*, *Leptinotarsa decemlineata*, *Diabrotica* spp., *Monochamusaltematus endai*, *Lissorhoptrusoryzophilus*, *Lyctus brunneus*.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus*, *Calliphora erythrocephala*, *Ceratitis capitata*, *Chironomus* spp., *Chrysomyia* spp., *Chrysops* spp., *Cochliomyia* spp., *Contarinia* spp., *Cordylobia anthropophaga*, *Culex* spp., *Culicoides* spp., *Culiseta* spp., *Cuterebra* spp., *Dacus oleae*, *Dasyneura* spp., *Delia* spp., *Dermatobia hominis*, *Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit*, *Pegomyia* spp., *Phlebotomus* spp., *Phorbia* spp., *Phormia* spp., *Prodiplosis* spp., *Psila rosae*, *Rhagoletis* spp., *Sarcophaga* spp., *Simulium* spp, *Stomoxys* spp., *Tabanus* spp., *Tannia* spp., *Tetanops* spp., *Tipula* spp. Additionally, *Musca domestica*, *Aedes aegypti*, *Delia platura*, *Culex pipiens pallens*, *Anopheles sinensis*, *Culex tritaeniorhynchus*, *Liriomyza trifolii*.

From the order of Hemiptera, for example, *Nephotettix cincticeps*, *Nilaparvata lugens*, *Pseudococcus comstocki*, *Unaspis yanonensis*, *Myzus persicas*, *Aphis pomi*, *Aphis gossypii*, *Lipaphis erysimi*, *Stephanitisnashi*, *Nezara* spp., *Trialeurodes vaporariorum*, *Psylla* spp.; Thysanoptera, for example, *Thrips palmi*, *Franklinella occidentalis*; Orthoptera pest, for example, *Gryllotalpa africana*, *Locusta migratoria*;

From the order of the Heteroptera, for example, *Anasa tristis*, *Antestiopsis* spp., *Boisea* spp., *Blissus* spp., *Calocoris* spp., *Campylomma livida*, *Cavelerius* spp., *Cimex* spp., *Cimex lectularius*, *Cimex hemipterus*, *Collaria* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Monalonion atratum*, *Nezara* spp., *Oebalus* spp., *Pentomidae*, *Piesma quadrata*, *Piezodorus* spp., *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Carneocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus*, *Ferrisia* spp., *Geococcus coffeae*, *Hieroglyphus* spp., *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva* spp., *Melanaphis sacchari*, *Metcalfiella* spp., *Metopolophium dirhodum*, *Monellia* costalis, Monelliopsis pecanis, Myzus spp., Nasonovia ribisnigri, Nephotettix spp., Nilaparvata lugens, Oncometopia spp., Orthezia praelonga, Parabemisia myricae, Paratrioza spp., Parlatoria spp., Pemphigus spp., Peregrinus maidis, Phenacoccus spp., Phloeomyzus passerinii, Phorodon humuli, Phylloxera spp., Pinnaspis aspidistrae, Planococcus spp., Protopulvinaria pyriformis, Pseudaulacaspis pentagona, Pseudococcus spp., Psylla spp., Pteromalus spp., Pyrilla spp., Quadraspidiotus spp., Quesada gigas, Rastrococcus spp., Rhopalosiphum spp., Saissetia spp., Scaphoides titanus, Schizaphis graminum, Selenaspidus articulatus, Sogata spp., Sogatella furcifera, Sogatodes spp., Stictocephala festina, Tenalaphara malayensis, Tinocallis caryaefoliae, Tomaspis spp., Toxoptera spp., Trialeurodes spp., Trioza spp., Typhlocyba spp., Unaspis spp., Viteus vitifolii, Zygina spp.

From the order of the Hymenoptera, for example, Acromyrmex spp., Athalia spp., Atta spp., Diprion spp., Hoplocampa spp., Lasius spp., Monomorium pharaonis, Solenopsis invicta, Tapinoma spp., Vespa spp.

From the order of the Isopoda, for example, Armadillidium vulgare, Oniscus asellus, Porcellio scaber.

From the order of the Isoptera, for example, Coptotermes spp., Cornitermes cumulans, Ctyptotermes spp., Incisitermes spp., Microtermes obesi, Odontotermes spp., Reticulitermes spp.

From the order of the Lepidoptera, for example, Acronicta major, Adoxophyes spp., Aedia leucomelas, Agrotis spp., Alabama spp., Amyelois transitella, Anarsia spp., Anticarsia spp., Argyroploce spp., Barathra brassicae, Borbo cinnara, Bucculatrix thurberiella, Bupalus piniarius, Busseola spp., Cacoecia spp., Caloptilia theivora, Capua reticulana, Carpocapsa pomonella, Carposina niponensis, Cheimatobia brumata, Chilo spp., Choristoneura spp., Clysia ambiguella, Cnaphalocerus spp., Cnephasia spp., Conopomorpha spp., Conotrachelus spp., Copitarsia spp., Cydia spp., Dalaca noctuides, Diaphania spp., Diatraea saccharalis, Earias spp., Ecdytolopha aurantium, Elasmopalpus lignosellus, Eldana saccharina, Ephestia spp., Epinotia spp., Epiphyas postvittana, Etiella spp., Eulia spp., Eupoecilia ambiguella, Euproctis spp., Euxoa spp., Feltia spp., Galleria mellonella, Gracillaria spp., Grapholitha spp., Hedylepta spp., Helicoverpa spp., Heliothis spp., Hofmannophila pseudospretella, Homoeosoma spp., Homona spp., Hyponomeuta padella, Kakivoria flavofasciata, Laphygma spp., Laspeyresia molesta, Leucinodes orbonalis, Leucoptera spp., Lithocolletis spp., Lithophane antennata, Lobesia spp., Loxagrotis albicosta, Lymantria spp., Lyonetia spp., Malacosoma neustria, Maruca testulalis, Mamestra brassicae, Mocis spp., Mythimna separata, Nymphula spp., Oiketicus spp., Oria spp., Orthaga spp., Ostrinia spp., Oulema oryzae, Panolis flammea, Parnara spp., Pectinophora spp., Perileucoptera spp., Phthorimaea spp., Phyllocnistis citrella, Phyllonorycter spp., Pieris spp., Platynota stultana, Plodia interpunctella, Plusia spp., Plutella xylostella, Prays spp., Prodenia spp., Protoparce spp., Pseudaletia spp., Pseudoplusia includens, Pyrausta nubilalis, Rachiplusia nu, Schoenobius spp., Scirpophaga spp., Scotia segetum, Sesamia spp., Sparganothis spp., Spodoptera spp., Stathmopoda spp., Stomopteryx subsecivella, Synanthedon spp., Tecia solanivora, Thermesia gemmatalis, Tinea pellionella, Tineola bisselliella, Tortrix spp., Trichophaga tapetzella, Trichoplusia spp., Tuta absoluta, Virachola spp. Additionally, Lymantria dispar, Malacosomaneustria, Pieris rapae crucivora, Spodoptera litura, Mamestra brassicae, Chilo suppressalis, Ostrinia nubilalis, Cadra cautella, Adoxophyes honmai, Cydia pomonella, Agrotis segetum, Galleria mellonella, Plutella xylostella, Heliothis virescens, and Phyllocnistis citrella;

Further, as mites, there are for example, Tetranychus cinnabarinus, Tetranychus urticae, Panonychus citri, Aculops pelekassi, Tarsonemus spp.

From the order of the Orthoptera, for example, Acheta domesticus, Blatta orientalis, Blattella germanica, Dichroplus spp., Gryllotalpa spp., Leucophaea maderae, Locusta spp., Melanoplus spp., Periplaneta spp., Pulex irritans, Schistocerca gregaria, Supella longipalpa.

From the order of the Siphonaptera, for example, Ceratophyllus spp., Ctenocephalides spp., Tunga penetrans, Xenopsylla cheopis.

From the order of the Symphyla, for example, Scutigerella spp.

From the order of the Thysanoptera, for example, Anaphothrips obscurus, Baliothrips biformis, Drepanothris reuteri, Enneothrips flavens, Frankliniella spp., Heliothrips spp., Hercinothrips femoralis, Rhipiphorothrips cruentatus, Scirtothrips spp., Taeniothrips cardamoni, Thrips spp.

From the order of the Zygentoma (=Thysanura), for example, Lepisma saccharina, Thennobia domestica, for example Lepisma saccharina, Thermobia domestica.

Order: Mollusca: From the class of the Bivalvia, for example, Dreissena spp.: From the class of the Gastropoda, for example, Anion spp., Biomphalaria spp., Bulinus spp., Deroceras spp., Galba spp., Lymnaea spp., Oncomelania spp., Pomacea spp., Suceinea spp.

Order: Plathelminthes, Nematodes (animal parasites): From the class of the Helminths, for example, Ancylostoma duodenale, Ancylostoma ceylanicum, Acylostoma braziliensis, Ancylostoma spp., Ascaris spp., Brugia malayi, Brugia timori, Bunostomum spp., Chabertia spp., Clonorchis spp., Cooperia spp., Dicrocoelium spp, Dictyocaulus filaria, Diphyllobothrium latum, Dracunculus medinensis, Echinococcus granulosus, Echinococcus multilocularis, Enterobius vermicularis, Faciola spp., Haemonchus spp., Heterakis spp., Hymenolepis nana, Hyostrongulus spp., Loa Loa, Nematodirus spp., Oesophagostomum spp., Opisthorchis spp., Onchocerca volvulus, Ostertagia spp., Paragonimus spp., Schistosomen spp, Strongyloides fuelleborni, Strongyloides stercoralis, Stronyloides spp., Taenia saginata, Taenia solium, Trichinella Trichinella nativa, Trichinella britovi, Trichinella nelsoni, Trichinella pseudopsiralis, Trichostrongulus spp., Trichuris trichuria, Wuchereria bancrofti.

Order: Nematodes (plant parasites, phytoparasites): From the group of the phytoparasitic nematodes, for example, Aphelenchoides spp., Bursaphelenchus spp., Ditylenchus spp., Globodera spp., Heterodera spp., Longidorus spp., Meloidogyne spp., Pratylenchus spp., Radopholus similis, Trichodorus spp., Tylenchulus semipenetrans, Xiphinema spp. Additionally, Meloidogyne incognita, Bursaphelenchus xylophilus, Aphelenchoides besseyi, Heterodera glycines, Pratylenchus spp.

Subphylum: Protozoa: It is furthermore possible to control protozoa, such as Eimeria In addition, the compounds of the present invention can be, used for controlling a wide variety of pests, including, for example, harmful sucking insects, biting insects and other plant-parasitic pests, stored grain pests, pests which destroy technical materials, and hygienic pests as well as pests, including parasites, in the veterinary field and can be applied for their control, like for example eradication and extermination. Therefore, the present invention also encompasses a method for controlling harmful pests.

Any kind of plant and plant part can be treated according to the present invention. In the present invention, a plant should be understood as all plants and plant populations including desirable and undesirable wild plants or crop plants (including naturally-occurring crop plants) and the like. As for the crop plants, they can be plants which are obtainable by conventional methods of breeding modified varieties and optimization methods, or biotechnological methods and genetic engineering methods, or by combination of these methods, and they include transgenic plants. In addition, plant varieties which are either protected or not protected by a plant breeder are also included. Plant parts should be understood as all parts and organs of a plant that are present above or under ground. Examples thereof include shoots, leaves, flowers and roots, etc. Specific examples thereof include a leaf, a needle-like leaf, a stem, a trunk, a flower, a fruit, a fruit body, a seed, a root, a tuber and an underground tuber, etc. Plant parts also include a harvested material and a material which propagates sexually or asexually, for example, a cutting, a tuber, an underground tuber, a side branch and a seed.

The arylpyrrolidine compounds according to the invention can be used for the treatment of seeds and thus the invention is also directed to the use of the arylpyrrolidine compounds according to the invention for the protection of seeds and plants emerging from seeds. The invention is also directed to a method of protecting seeds and plants emerging from seeds by treating the seeds with a compound, or a pesticidal composition according to the invention. It is understood that seeds from conventional plants as well as seeds from genetically modified plants can be treated with the compounds or the pesticidal composition according to the invention.

Treatment of plants and plant parts (including seeds) with the arylpyrrolidine compounds or the pesticidal composition according to the present invention can be carried out directly or by using conventional methods such as impregnation, spray, evaporation, particularization, dispersion, coating and injection, or for a propagating material, especially for a seed, by coating it with one or more of the compounds, so that the compounds are applied to their surroundings, habitat environment, or preservation place.

The compounds of the present invention have a penetrating activity and this means that the compounds can penetrate a plant body and can migrate from the underground part to the above-ground part of a plant.

As it has been described herein, according to the present invention, all plants and parts thereof can be treated. According to a preferred embodiment for carrying out the invention, wild plant species and plant mutants, or those obtained by traditional plant breeding methods such as hybridization or protoplast fusion, and parts thereof are treated. According to a more preferred embodiment for carrying out the invention, transgenic plants and plant varieties (genetically modified organisms) obtained by conventional methods in appropriate combination with genetic engineering methods, and parts thereof are treated. The terms "parts", "parts of a plant" and "plant parts" are as defined above.

Still more preferably, for each specific case, plants of plant varieties that are commercially available or currently in use are treated according to the present invention. Plant varieties are understood as plants having new characteristics ("traits") obtained by conventional breed improvements, introduction of mutation or recombinant DNA techniques. They can be plant varieties, biotypes or genotypes.

Depending on plant species or plant varieties, their habitat and growth condition (soil, weather, growth period, nutrition, etc.), the treatment according to the present invention may have a supra-additive ("synergy") effect. Thus, for example, exceeding an expected effect, it is possible to obtain several effects including reduction of application rate and/or broadening of an activity spectrum, and/or increased activity of the material and composition that can be used according to the present invention, improvement of plant growth, enhancement of tolerance to high or low temperature, enhancement of tolerance to drought, moisture or salt contained in soil, improvement of a flowering property, simplification of harvest methods, accelerated maturation, increased harvest amount, improvement of quality and/or nutritional value of harvest products, and improvement of preservation stability and/or processability of harvested products.

The preferable transgenic plants or plant varieties (obtainable by genetic engineering methods) treated according to the present invention include all kinds of plant having genetic materials that can provide the plants with very advantageous and useful traits based on genetic modifications. Examples of such traits include improvement of plant growth, enhancement of tolerance to high or low temperature, enhancement of tolerance to drought, moisture or salt contained in soil, improvement of a flowering property, simplification of harvest methods, accelerated maturation, increased harvest amount, improvement of quality and/or nutritional value of harvest products, and improvement of preservation stability and/or processability of harvested products. Further examples in which such traits are particularly more emphasized include improved protection of plants against harmful animals and harmful microorganisms such as insect, tick, plant pathogenic fungus, bacteria and/or virus, and improved tolerance of plants against compounds having certain type of herbicidal activities. Examples of the transgenic plant include grain crops (barley, rice), corn, soybean, potato, sugar beet, tomato, bean and other modified plant species, useful plants such as cotton, tobacco, rape, and fruit plants (fruits like an apple, a pear, a citrus fruit and other fruit-bearing plants like a grape). In particular, corn, soybean, potato, cotton, tobacco and rape are important. As for the traits considered to be important, improved plant defense based on toxins produced by plants, in particular based on the toxins produced by plants with an action of genetic materials derived from *Bacillus thuringiensis* (for example, genes including CryIA(a), CryIA (b), CryIA(c), CryIIA, CryIIIA, CryIIIB2, Cry9c, Cry2Ab, Cry3Bb and CryIF, and combination thereof), against insects, spider-like animals, nematodes, slugs, and snails (herein, referred to as "Bt plant") can be mentioned. Other traits considered to be important include improved plant defense against fungus, bacteria and virus, based on systemic acquired resistance (SAR), systemin, phytoallexin, elicitor, resistance gene and the corresponding protein and toxin expressed from the gene. Further, particularly important traits are improved tolerance of plants to a certain kind of an active compound having a herbicidal activity, such as imidazolinone, sulfonyl urea, glyphosate or phosphinotricine (e.g., "PTA" gene). Genes which can endow desired traits to a subject can also be present in combination each other in a transgenic plant. Examples of the "Bt plant" include modified varieties of corn, modified varieties of cotton and modified varieties of potato that are commercially available under the trade names of YIELD GARD® (for example, corn, cotton, soybean), KnockOut® (for example, corn), StarLink® (for example, corn), Bollgard® (cotton), Nucotn® (cotton) and New Leaf® (potato), respectively. Examples of the plant having resistance to herbicides include modified varieties of corn, modified varieties of cotton and modified varieties of potato that are commercially available under the trade names of Roundup Ready® (resistance to glyphosate, for example, corn, cotton, soybean), Liberty Link® (resistance to phosphinotricine, for example rape), IMI® (resistance to imidazolinones) and STS® (resistance to sulfonyl urea, for example, corn), respectively. Examples of the plant having resistance to herbicides (i.e., the plant obtained by conventional breeding methods to have resistance to herbicides) also include modified varieties, for example those that are commercially available under the trade name of Clearfield® (for example, corn). Of course, these descriptions are also applied to plant varieties which have already had genetic traits or will have genetic traits to be developed in future. Such plant varieties will be developed and/or on the market in future.

With the compounds of the present invention at appropriate concentration, the plants mentioned above can be advantageously treated.

When used as pesticides, the active compounds of the present invention can be prepared in a form of common preparation (pesticidal compositions). Such preparation form may includes, for example, a solution, an emulsion, wettable powder, granulated wettable powder, a suspension, powder, a foam, a paste, a tablet, a granule, an aerosol, a natural or synthetic agent impregnated with the active compounds, a microcapsule, a coating agent for seeds, a formulation equipped with a combustion device (the combustion device can be a smoke or fog cartridge, a can or a coil, etc.) and ULV (cold mist, warm mist), and the like.

These formulations may be prepared by methods known per se. For example, they can be prepared by mixing the active compounds together with spreading agents, i.e. liquid diluents or carriers; liquefied gas diluents or carriers; solid diluents or carriers, and, optionally, with surfactants i.e. emulsifiers and/or dispersants and/or foam-forming agents.

When water is used as a spreading agent, for example, organic solvents may be used as auxiliary solvents.

Liquid diluents or carriers may include: for example, aromatic hydrocarbons (e.g. xylene, toluene, alkylnaphthalene etc.), chlorinated aromatic or chlorinated aliphatic hydrocarbons (e.g. chlorobenzenes, ethylene chlorides, methylene chlorides etc.), aliphatic hydrocarbons (e.g. cyclohexanes) or paraffins (e.g. mineral oil fractions), alcohols (e.g. butanol, glycol and ethers or esters thereof, etc.), ketones (e.g. acetone, methyl ethyl ketone, methyl isobutyl ketone, cyclohexanone etc.), strong polar solvents (e.g. dimethylformamide, dimethylsulfoxide etc.), water and the like.

Liquefied gas diluents or carriers may include those present as gas at atmospheric temperature and by evaporation, for example, butane, propane, nitrogen gas, carbon dioxide, and an aerosol propellant such as halogenated hydrocarbons.

Examples of the solid diluents include ground natural minerals (for example, kaolins, clay, talc, chalk, quartz, attapulgite, montmorillonite, diatomaceous earth, etc.) and finely-ground synthetic minerals (for example, highly dispersed silicic acid, alumina and silicate, etc.) and the like.

Examples of the solid carriers for granules may include finely pulverized and sifted rocks (for example, calcite, marble, pumice, sepiolite and dolomite, etc.), synthetic granules of inorganic or organic powders, and fine granules of organic materials (for example, sawdust, coconut shells, corn cobs and tobacco stalks, etc.) and the like.

Examples of the emulsifiers and/or foam formers may include nonionic and anionic emulsifiers, for example, polyoxyethylene fatty acid esters, polyoxyethylene fatty acid alcohol ethers (for example, alkylaryl polyglycol ether), alkyl sulfonates, alkyl sulfates and aryl sulfonates, and albumin hydrolysates and the like.

Examples of the dispersants include lignin sulfite waste liquor and methylcellulose.

Binders may also be used in the formulation (powder, granule and emulsion). Examples of the binders may include carboxymethyl cellulose, natural or synthetic polymers (for example, gum arabic, polyvinyl alcohol and polyvinyl acetate, etc.).

Colorants may also be used. Examples of the colorants may include inorganic pigments (for example, iron oxide, titanium oxide and Prussian blue, etc.), organic dyes such as Alizarin dyes, azo dyes or metal phthalocyanine dyes, and further, trace elements such as salts of iron, manganese, boron, copper, cobalt, molybdenum or zinc.

In general, the formulation may include the above active components in an amount of 0.1 to 95% by weight, preferably 0.5 to 90% by weight.

The compounds of the present invention can be provided as mixtures with other active compounds such as pesticides, poison baits, sterilizing agents, acaricidal agents, nematocides, fungicides, growth regulating agents, and herbicides in a form of commercially useful formulation or an application form modified from formulation thereof.

The amount of the compounds of the present invention in commercially useful application form may vary over a broad range.

The concentration of the active compounds of the present invention for actual use may be, for example, between 0.0000001 and 100% by weight, preferably between 0.00001 and 1% by weight.

The compounds of the present invention can be used according to any common methods suitable for each application form.

The compounds of the present invention have stability that is effective for alkaline substances present on lime materials when the compounds are used against hygienic pests and other stored product pests. In addition, they exhibit excellent residual effectiveness on woods and soils.

In the veterinary fields, i.e. in the field of veterinary medicine, the active compounds according to the present invention are active against animal parasites, in particular ectoparasites or endoparasites. The term endoparasites includes in particular helminths, such as cestodes, nematodes or trematodes, and protozoae, such as coccidia. Ectoparasites are typically and preferably arthropods, in particular insects such as flies (stinging and licking), parasitic fly larvae, lice, hair lice, bird lice, fleas and the like; or acarids, such as ticks, for examples hard ticks or soft ticks, or mites, such as scab mites, harvest mites, bird mites and the like.

These parasites include:

From the order of the Anoplurida, for example *Haematopinus* spp., *Linognathus* spp., *Pediculus* spp., *Phtirus* spp., *Solenopotes* spp.; particular examples are: *Linognathus setosus, Linognathus vituli, Linognathus ovillus, Linognathus oviformis, Linognathus pedalis, Linognathus stenopsis, Haematopinus asini macrocephalus, Haematopinus eurysternus, Haematopinus suis, Pediculus humanus capitis, Pediculus humanus corporis, Phylloera vastatrix, Phthirus pubis, Solenopotes capillatus;*

From the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; particular examples are: *Bovicola bovis, Bovicola ovis, Bovicola limbata, Damalina bovis, Trichodectes canis, Felicola subrostratus, Bovicola caprae, Lepikentron ovis, Werneckiella equi;*

From the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp.,

*Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; particular examples are: *Aedes aegypti, Aedes albopictus, Aedes taeniorhynchus, Anopheles gambiae, Anopheles maculipennis, Calliphora erythrocephala, Chrysozona pluvialis, Culex quinquefasciatus, Culex pipiens, Culex tarsalis, Fannia canicularis, Sarcophaga carnaria, Stomoxys calcitrans, Tipula paludosa, Lucilia cuprina, Lucilia sericata, Simulium reptans, Phlebotomus papatasi, Phlebotomus longipalpis, Odagmia ornata, Wilhelmia equina, Boophthora erythrocephala, Tabanus bromius, Tabanus spodopterus, Tabanus atratus, Tabanus sudeticus, Hybomitra ciurea, Chrysops caecutiens, Chrysops relictus, Haematopota pluvialis, Haematopota italica, Musca autumnalis, Musca domestica, Haematobia irritans irritans, Haematobia irritans exigua, Haematobia stimulans, Hydrotaea irritans, Hydrotaea albipuncta, Chrysomya chloropyga, Chrysomya bezziana, Oestrus ovis, Hypoderma bovis, Hypoderma lineatum, Przhevalskiana silenus, Dermatobia hominis, Melophagus ovinus, Lipoptena capreoli, Lipoptena cervi, Hippobosca variegata, Hippobosca equina, Gasterophilus intestinalis, Gasterophilus haemorroidalis, Gasterophilus inermis, Gasterophilus nasalis, Gasterophilus nigricornis, Gasterophilus pecorum, Braula coeca*;

From the order of the Siphonapterida, for example *Pulex* spp., *Ctenocephalides* spp., *Tunga* spp., *Xenopsylla* spp., *Ceratophyllus* spp.; particular examples are: *Ctenocephalides canis, Ctenocephalides felis, Pulex irritans, Tunga penetrans, Xenopsylla cheopis*;

From the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp. (e.g. *Suppella longipalpa*);

From the subclass of the Acari (Acarina) and the orders of the Meta- and Mesostigmata, for example *Argas* spp., *Ornithodorus* spp., *Otobius* spp., *Ixodes* spp., *Amblyomma* spp., *Rhipicephalus (Boophilus)* spp *Dermacentor* spp., *Haemophysalis* spp., *Hyalomma* spp., *Dermanyssus* spp., *Rhipicephalus* spp. (the original genus of multi host ticks) *Ornithonyssus* spp., *Pneumonyssus* spp., *Raillietia* spp., *Pneumonyssus* spp., *Sternostoma* spp., *Varroa* spp., *Acarapis* spp.; particular examples are: *Argas persicus, Argas reflexus, Ornithodorus moubata, Otobius megnini, Rhipicephalus (Boophilus) microplus, Rhipicephalus (Boophilus) decoloratus, Rhipicephalus (Boophilus) annulatus, Rhipicephalus (Boophilus) calceratus, Hyalomma anatolicum, Hyalomma aegypticum, Hyalomma marginatum, Hyalomma transiens, Rhipicephalus evertsi, Ixodes ricinus, Ixodes hexagonus, Ixodes canisuga, Ixodes pilosus, Ixodes rubicundus, Ixodes scapularis, Ixodes holocyclus, Haemaphysalis concinna, Haemaphysalis punctata, Haemaphysalis cinnabarina, Haemaphysalis otophila, Haemaphysalis leachi, Haemaphysalis longicorni, Dermacentor marginatus, Dermacentor reticulatus, Dermacentor pictus, Dermacentor albipictus, Dermacentor andersoni, Dermacentor variabilis, Hyalomma mauritanicum, Rhipicephalus sanguineus, Rhipicephalus bursa, Rhipicephalus appendiculatus, Rhipicephalus capensis, Rhipicephalus turanicus, Rhipicephalus zambeziensis, Amblyomma americanum, Amblyomma variegatum, Amblyomma maculatum, Amblyomma hebraeum, Amblyomma cajennense, Dermanyssus gallinae, Ornithonyssus bursa, Ornithonyssus sylviarum, Varroa jacobsoni*;

From the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.; particular examples are: *Cheyletiella yasguri, Cheyletiella blakei, Demodex canis, Demodex bovis, Demodex ovis, Demodex caprae, Demodex equi, Demodex caballi, Demodex suis, Neotrombicula autumnalis, Neotrombicula desaleri, Neoschongastia xerothermobia, Trombicula akamushi, Otodectes cynotis, Notoedres cati, Sarcoptis canis, Sarcoptes bovis, Sarcoptes ovis, Sarcoptes rupicaprae (=S. caprae), Sarcoptes equi, Sarcoptes suis, Psoroptes ovis, Psoroptes cuniculi, Psoroptes equi, Chorioptes bovis, Psoergates ovis, Pneumonyssoidic mange, Pneumonyssoides caninum, Acarapis woodi.*

The active compounds according to the invention are also suitable for controlling arthropods, helminths and protozoae, which attack animals. Animals include agricultural livestock such as, for example, cattle, sheep, goats, horses, pigs, donkeys, camels, buffaloes, rabbits, chickens, turkeys, ducks, geese, cultured fish, honeybees. Moreover, animals include domestic animals—also referred to as companion animals—such as, for example, dogs, cats, cage birds, aquarium fish and what are known as experimental animals such as, for example, hamsters, guinea pigs, rats and mice.

By controlling these arthropods, helminths and/or protozoae, it is intended to reduce deaths and improve performance (in the case of meat, milk, wool, hides, eggs, honey and the like) and health of the host animal, so that more economical and simpler animal keeping is made possible by the use of the active compounds according to the invention.

For example, it is desirable to prevent or interrupt the uptake of blood by the parasites from the hosts (when applicable). Also, controlling the parasites may help to prevent the transmittance of infectious agents.

The term "controlling" as used herein with regard to the veterinary field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Generally, when used for the treatment of animals the active compounds according to the invention can be applied directly. Preferably they are applied as pharmaceutical compositions which may contain pharmaceutically acceptable excipients and/or auxiliaries which are known in the art.

In the veterinary field and in animal keeping, the active compounds are applied (=administered) in the known manner by enteral administration in the form of, for example, tablets, capsules, drinks, drenches, granules, pastes, boluses, the feed-through method, suppositories; by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-compound-comprising shaped articles such as collars, ear tags, tail tags, limb bands, halters, marking devices and the like. The active compounds may be formulated as shampoo or as suitable formulations usable in aerosols, unpressurized sprays, for example pump sprays and atomizer sprays.

When used for livestock, poultry, domestic animals and the like, the active compounds according to the invention can be applied as formulations (for example powders, wettable powders ["WP"], emulsions, emulsifiable concentrates ["EC"], flowables, homogeneous solutions, and suspension concentrates ["SC"]) which comprise the active compounds in an amount of from 1 to 80% by weight, either directly or after dilution (e.g. 100- to 10 000-fold dilution), or else as a chemical bath.

When used in the veterinary field the active compounds according to the invention may be used in combination with suitable synergists or other active compounds, such as for example, acaricides, insecticides, anthelmintics, anti-protozoal drugs.

The compounds according to the invention can be prepared as illustrated below:

1. Synthesis of N-[(1S)-1-(4-{3-[3,5-bis(trifluoromethyl)phenyl]-3-(trifluoromethyl)pyrrolidin-1-yl}phenyl)ethyl]cyclopropanecarboxamide (compound no. 11-b)

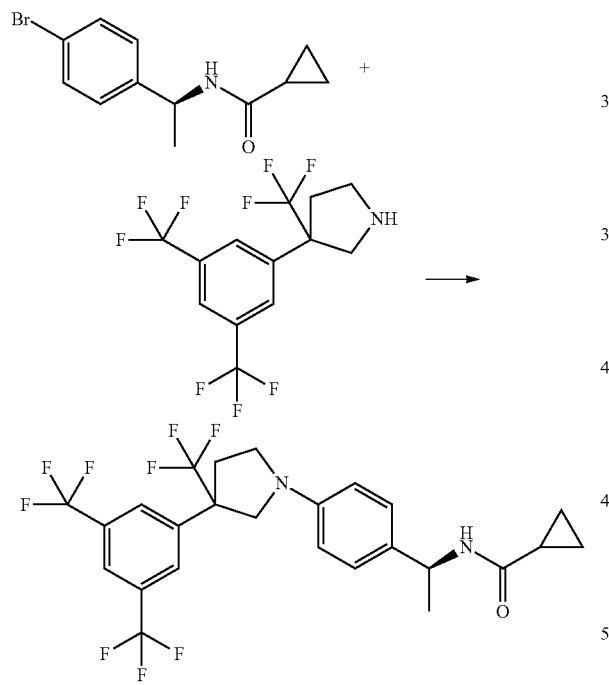

To a reaction vessel, N-[(1S)-1-(4-bromophenyl)ethyl]cyclopropanecarboxamide (134 mg), 3-[3,5-bis(trifluoromethyl)phenyl]-3-(trifluoromethyl)pyrrolidine (211 mg), sodium t-butoxide (96 mg), tris(dibenzylideneacetone)dipalladium(0)-chloroform adduct (10 mg), 4,5-bis(diphenylphosphino)-9,9-dimethylxanthene (18 mg) and toluene (6 ml) were added, and reacted in a microwave reactor (Initiator™, manufactured by Biotage) for 10 minutes at 120° C. Upon the completion of the reaction, ethyl acetate was added and the precipitates were filtered by using silica gel. The solvent was distilled off under reduced pressure and the residue was purified by silica gel column chromatography to obtain N-[(1S)-1-(4-{3-[3,5-bis-(trifluoromethyl)phenyl]-3-(trifluoromethyl)pyrrolidin-1-yl}phenyl)ethyl]cyclopropanecarboxamide (269 mg). $^1$H-NMR (CDCl$_3$) as given in Table 2

2. Synthesis of N-[(1S)-1-(4-{3-[2,6-bis(trifluoromethyl)pyridin-4-yl]-3-(trifluoromethyl)pyrrolidin-1-yl}phenyl)ethyl]cyclopropanecarboxamide (compound no. 17-b)

(1) Method for Preparing Compounds of Formula (II)—Step (i)

Synthesis of 4-[1-benzyl-3-(trifluoromethyl)pyrrolidin-3-yl]-2,6-bis(trifluoromethyl)pyridine

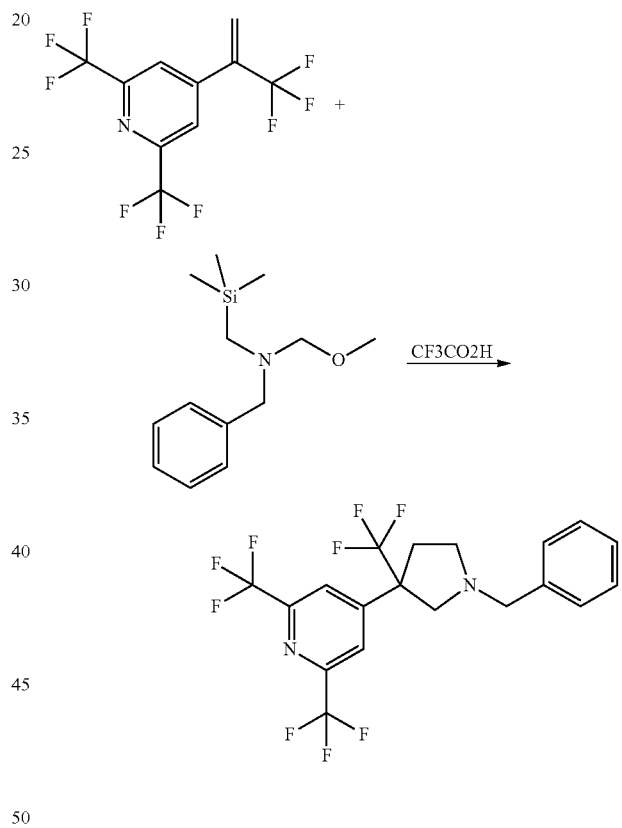

To the solution of 2,6-bis(trifluoromethyl)-4-(3,3,3-trifluoroprop-1-en-2-yl)pyridine (1.25 g) and N-benzyl-1-methoxy-N-[(trimethylsilyl)methyl]methanamine (5.0 g) in dichloromethane was added dropwise the solution of trifluoroacetic acid (0.038 g) in dichloromethane while cooling with ice. On completion of the dropwise addition, the mixture was warmed to room temperature and stirred over night. The mixture was washed with saturated sodium bicarbonate water and dried over anhydrous magnesium sulfate. After the drying agent was filtered off, the solvent was distilled away under the reduced pressure, and the residue was then purified by silica gel chromatography to yield 4-[1-benzyl-3-(trifluoromethyl)pyrrolidin-3-yl]-2,6-bis(trifluoromethyl)pyridine (1.52 g). $^1$H-NMR (CDCl$_3$) δ: 2.23-2.29 (1H, m), 2.65-2.69 (2H, m), 2.96 (1H, d), 3.05-3.15 (2H, m), 3.58 (1H, d), 3.82 (1H, d), 7.26-7.37 (5H, m), 8.00 (2H, s).

(2) Method for Preparing Compounds of Formula (II)—Step (ii)

Synthesis of 2,6-bis(trifluoromethyl)-4-[3-(trifluoromethyl)pyrrolidin-3-yl]pyridine

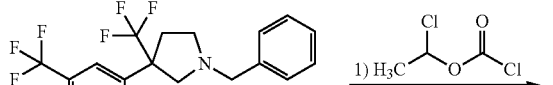

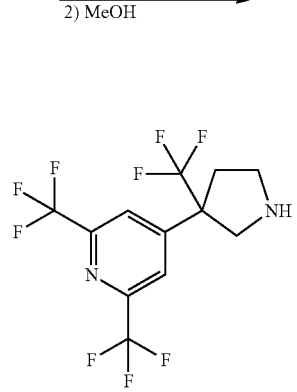

The solution of 4-[1-benzyl-3-(trifluoromethyl)pyrrolidin-3-yl]-2,6-bis(trifluoromethyl)pyridine (1.4 g) and 1-chloroethyl chloroformate (0.905 g) in dichloroethane was heated to reflux for 3 hours. The mixture was cooled to room temperature and then concentrated under the reduced pressure. Methanol was added to the resultant residue, which was then heated with stirring at 60° C. for two hours. The mixture was cooled to room temperature, to which was then added water. The solution was washed twice with the mixed solvent of hexane. The solution was neutralized with sodium hydroxide and then extracted with tert-butyl methyl ether three times. The organic layer was combined, which was then washed with brine and dried over anhydrous magnesium sulfate. After the drying agent was filtered off, the solvent was distilled away under the reduced pressure to yield 2,6-bis(trifluoromethyl)-4-[3-(trifluoromethyl)pyrrolidin-3-yl]pyridine (0.781 g).

$^1$H-NMR (CDCl$_3$) δ: 1.86 (1H, br s), 2.27-2.36 (1H, m), 2.63-2.69 (1H, m), 3.05-3.14 (1H, m), 3.26-3.33 (2H, m), 3.83 (1H, d), 7.87 (2H, s).

(3) Method for Preparation of Compounds According to the Invention: Preparation Method (a):

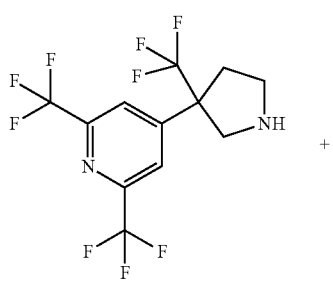

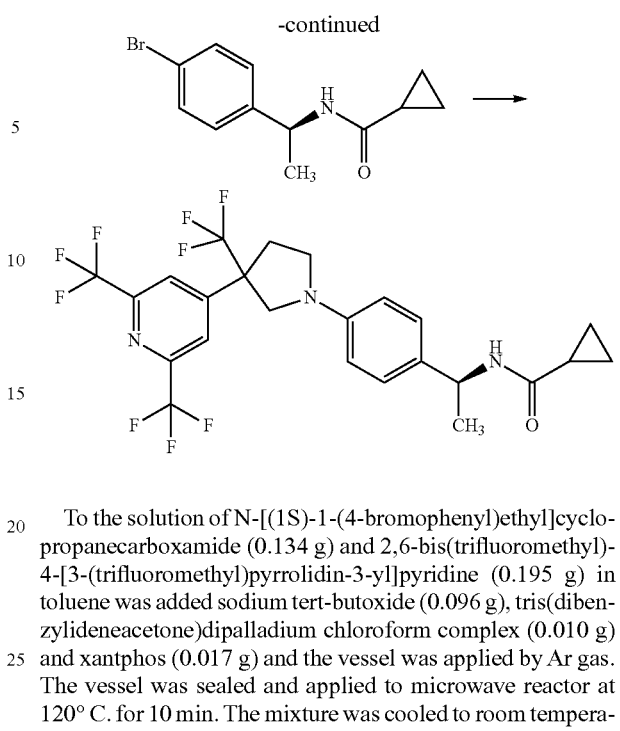

To the solution of N-[(1S)-1-(4-bromophenyl)ethyl]cyclopropanecarboxamide (0.134 g) and 2,6-bis(trifluoromethyl)-4-[3-(trifluoromethyl)pyrrolidin-3-yl]pyridine (0.195 g) in toluene was added sodium tert-butoxide (0.096 g), tris(dibenzylideneacetone)dipalladium chloroform complex (0.010 g) and xantphos (0.017 g) and the vessel was applied by Ar gas. The vessel was sealed and applied to microwave reactor at 120° C. for 10 min. The mixture was cooled to room temperature and then poured into water, which was then extracted twice with ethyl acetate. The organic layer was combined, which was then washed with water and dried over anhydrous magnesium sulfate. After the drying agent was filtered off, the solvent was distilled away under the reduced pressure, and the residue was then purified by silica gel chromatography to yield N-[(1S)-1-(4-{3-[2,6-bis(trifluoromethyl)pyridin-4-yl]-3-(trifluoromethyl)pyrrolidin-1-yl}phenyl)ethyl]cyclopropanecarboxamide (0.272 g).

$^1$H-NMR (CDCl$_3$) δ: 0.64-0.77 (2H, m), 0.86-1.01 (2H, m), 1.25-1.31 (1H, m), 1.48 (3H, d), 2.53-2.63 (1H, m), 2.91-3.00 (1H, m), 3.48-3.62 (2H, m), 3.85 (1H, d), 4.11 (1H, d), 5.03-5.13 (1H, m), 5.80 (1H, d), 6.62 (2H, d), 7.27 (2H, d), 7.90 (2H, s).

Compounds of below mentioned formulae A, B, C, D, E, F, G, H, and J, wherein R has the meaning as given in table 1 can obtained by the same or analogous preparation methods as described before, as example, without restricting the invention to those compounds.

TABLE 1

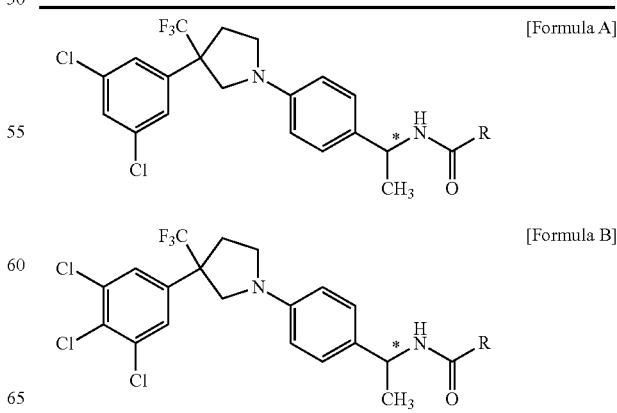

TABLE 1-continued

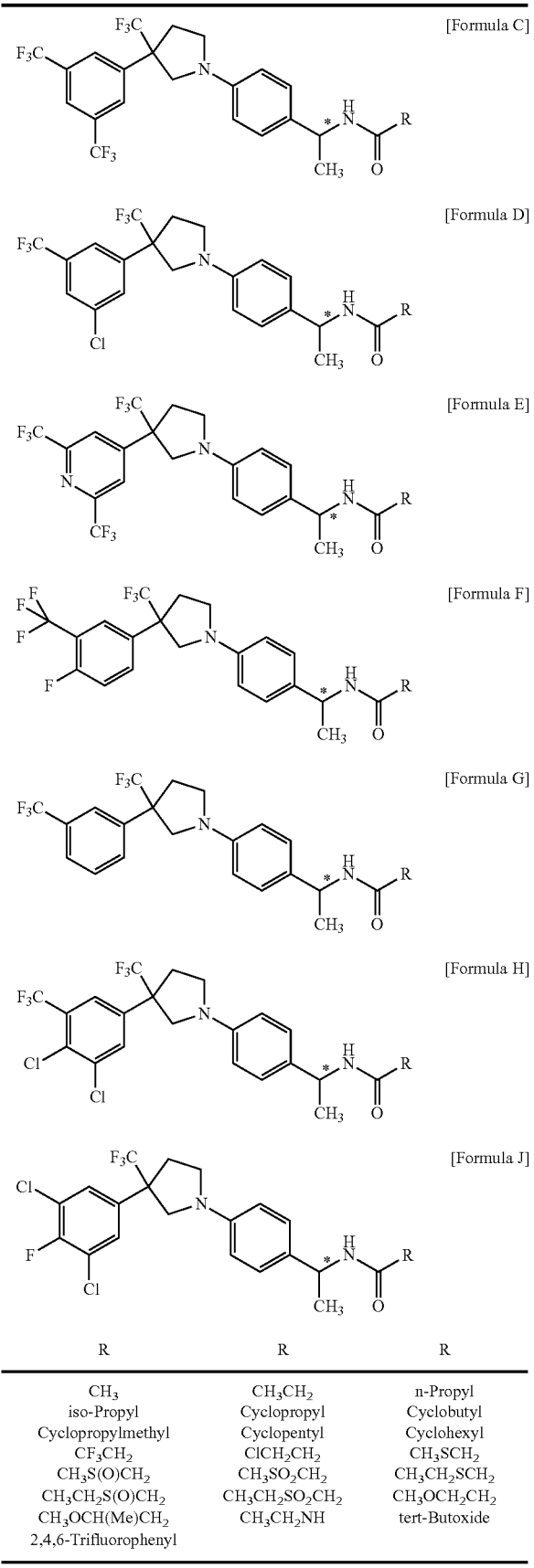

[Formula C]
[Formula D]
[Formula E]
[Formula F]
[Formula G]
[Formula H]
[Formula J]

| R | R | R |
|---|---|---|
| CH₃ | CH₃CH₂ | n-Propyl |
| iso-Propyl | Cyclopropyl | Cyclobutyl |
| Cyclopropylmethyl | Cyclopentyl | Cyclohexyl |
| CF₃CH₂ | ClCH₂CH₂ | CH₃SCH₂ |
| CH₃S(O)CH₂ | CH₃SO₂CH₂ | CH₃CH₂SCH₂ |
| CH₃CH₂S(O)CH₂ | CH₃CH₂SO₂CH₂ | CH₃OCH₂CH₂ |
| CH₃OCH(Me)CH₂ | CH₃CH₂NH | tert-Butoxide |
| 2,4,6-Trifluorophenyl | | |

In the tables, the compound number carrying "-a" or "-b" denotes the following:

"-a" means the compound in (R)-configuration. Such compounds are synthesized using preparation method (a) via compounds of formula (III) synthesized from (R)-(+)-1-(4-bromophenyl)ethylamine.

"-b" means the compound in (S)-configuration. Such compounds are synthesized using preparation method (a) via compounds of formula (III) synthesized from (S)-(−)-1-(4-bromophenyl)ethylamine.

TABLE 2

(I)

| Compound No. | $X^2$ | A | $X^4$ | $R^4$ |
|---|---|---|---|---|
| 1 | Cl | C—H | Cl | CH₃ |
| 1-b | Cl | C—H | Cl | CH₃ |
| 2 | Cl | C—H | Cl | CH₃CH₂ |
| 2-b | Cl | C—H | Cl | CH₃CH₂ |
| 3 | Cl | C—H | Cl | cyclo-Pr |
| 3-b | Cl | C—H | Cl | cyclo-Pr |
| 4 | Cl | C—H | CF₃ | CH₃CH₂ |
| 4-b | Cl | C—H | CF₃ | CH₃CH₂ |
| 5 | Cl | C—H | CF₃ | cyclo-Pr |
| 5-b | Cl | C—H | CF₃ | cyclo-Pr |
| 6 | Cl | C—Cl | Cl | CH₃ |
| 6-b | Cl | C—Cl | Cl | CH₃ |
| 7 | Cl | C—Cl | Cl | CH₃CH₂ |
| 7-a | Cl | C—Cl | Cl | CH₃CH₂ |
| 7-b | Cl | C—Cl | Cl | CH₃CH₂ |
| 8 | Cl | C—Cl | Cl | cyclo-Pr |
| 8-b | Cl | C—Cl | Cl | cyclo-Pr |
| 9 | CF₃ | C—H | CF₃ | CH₃ |
| 9-b | CF₃ | C—H | CF₃ | CH₃ |
| 10 | CF₃ | C—H | CF₃ | CH₃CH₂ |
| 10-a | CF₃ | C—H | CF₃ | CH₃CH₂ |
| 10-b | CF₃ | C—H | CF₃ | CH₃CH₂ |
| 11 | CF₃ | C—H | CF₃ | cyclo-Pr |
| 11-b | CF₃ | C—H | CF₃ | cyclo-Pr |
| 12 | Cl | C—Cl | Cl | cyclo-PrCH₂ |
| 12-b | Cl | C—Cl | Cl | cyclo-PrCH₂ |
| 13 | CF₃ | C—H | CF₃ | cyclo-PrCH₂ |
| 13-b | CF₃ | C—H | CF₃ | cyclo-PrCH₂ |
| 14 | Cl | C—Cl | Cl | CH₃OCH₂CH₂ |
| 14-b | Cl | C—Cl | Cl | CH₃OCH₂CH₂ |
| 15-b | CF₃ | C—H | CF₃ | CH₃OCH₂CH₂ |
| 16-b | CF₃ | C—H | CF₃ | 2,4,6-trifluorophenyl |
| 17-b | CF₃ | N | CF₃ | cyclo-Pr |

TABLE 3

| Compound No. | NMR |
|---|---|
| 1 | 1H-NMR (CDCl3) δ: 1.48 (3H, d), 1.94 (3H, s), 2.50-2.63 (1H, m), 2.79-2.87 (1H, m), 3.46-3.53 (2H, m), 3.77 (1H, d), 4.03 (1H, d), 5.05-5.10 (1H, m), 5.58 (1H, br s), 6.58 (2H, d), 7.18-7.47 (5H, m). |
| 1-b | 1H-NMR (CDCl3) δ: 1.48 (3H, d), 1.96 (3H, s), 2.52-2.55 (1H, m), 2.79-2.87 (1H, m), 3.45-3.55 (2H, m), 3.77 (1H, d), 4.03 (1H, d), 5.05-5.07 (1H, m), 5.59 (1H, d), 6.58 (2H, d), 7.25-7.36 (5H, m). |
| 2 | 1H-NMR (CDCl3) δ: 1.13-1.15 (3H, m), 1.47 (3H, d), 2.16-2.19 (2H, m), 2.51-2.53 (1H, m), 2.79-2.84 (1H, m), 3.46-3.52 (2H, m), 3.76 (1H, d), 4.02 (1H, d), 5.06-5.08 (1H, m), 5.62 (1H, d), 6.57 (2H, d), 7.27-7.33 (5H, m). |
| 2-b | 1H-NMR (CDCl3) δ: 1.14-1.16 (3H, m), 1.47 (3H, d), 2.17-2.22 (2H, m), 2.51-2.53 (1H, m), 2.78-2.87 (1H, m), 3.47-3.53 (2H, m), 3.77 (1H, d), 4.02 (1H, d), 5.05-5.12 (1H, m), 5.58 (1H, d), 6.58 (2H, d), 7.17-7.46 (5H, m). |
| 3 | 1H-NMR (CDCl3) δ: 0.66-0.73 (2H, m), 0.95-0.97 (2H, m), 1.23-1.31 (1H, m), 1.49 (3H, d), 2.50-2.54 (1H, m), 2.80-2.85 (1H, m), 3.47-3.53 (2H, m), 3.77 (1H, d), 4.03 (1H, d), 5.06-5.09 (1H, m), 5.78 (1H, br s), 6.58 (2H, d), 7.24-7.40 (5H, m). |
| 3-b | 1H-NMR (CDCl3) δ: 0.69-0.71 (2H, m), 0.96-0.97 (2H, m), 1.25-1.29 (1H, m), 1.50 (3H, d), 2.53-2.56 (1H, m), 2.80-2.85 (1H, m), 3.47-3.53 (2H, m), 3.77 (1H, d), 4.03 (1H, d), 5.06-5.09 (1H, m), 5.75 (1H, d), 6.58 (2H, d), 7.24-7.40 (5H, m). |
| 4 | 1H-NMR (CDCl3) δ: 1.05-1.17 (3H, m), 1.47 (3H, d), 2.17-2.19 (2H, m), 2.53-2.61 (1H, m), 2.85-2.93 (1H, m), 3.47-3.60 (2H, m), 3.80 (1H, d), 4.09 (1H, d), 5.03-5.12 (1H, m), 5.57 (1H, d), 6.59 (2H, d), 7.22 (2H, d), 7.59 (3H, t). |
| 4-b | 1H-NMR (CDCl3) δ: 1.14-1.16 (3H, m), 1.48 (3H, d), 2.14-2.22 (2H, m), 2.53-2.63 (1H, m), 2.85-2.93 (1H, m), 3.49-3.55 (2H, m), 3.80 (1H, d), 4.09 (1H, d), 5.06-5.08 (1H, m), 5.59 (1H, d), 6.59 (2H, d), 7.24 (2H, d), 7.59 (3H, t). |
| 5 | 1H-NMR (CDCl3) δ: 0.67-0.73 (2H, m), 0.93-0.99 (2H, m), 1.26-1.29 (1H, m), 1.48 (3H, d), 2.54-2.63 (1H, m), 2.85-2.93 (1H, m), 3.49-3.55 (2H, m), 3.80 (1H, d), 4.09 (1H, d), 5.06-5.08 (1H, m), 5.77 (1H, d), 6.60 (2H, d), 7.25 (2H, d), 7.59 (3H, t). |
| 5-b | 1H-NMR (CDCl3) δ: 0.69-0.71 (2H, m), 0.96-0.97 (2H, m), 1.24-1.31 (1H, m), 1.49 (3H, d), 2.55-2.62 (1H, m), 2.85-2.93 (1H, m), 3.50-3.58 (2H, m), 3.80 (1H, d), 4.09 (1H, d), 5.07-5.09 (1H, m), 5.75 (1H, d), 6.60 (2H, d), 7.29 (2H, d), 7.61 (3H, t). |
| 6 | 1H-NMR (CDCl3) δ: 1.48 (3H, d), 1.97 (3H, s), 2.50-2.52 (1H, m), 2.79-2.83 (1H, m), 3.45-3.55 (2H, m), 3.76 (1H, d), 4.01 (1H, d), 5.05-5.07 (1H, m), 5.58 (1H, br s), 6.58 (2H, d), 7.24 (2H, d), 7.43 (2H, s). |
| 6-b | 1H-NMR (CDCl3) δ: 1.48 (3H, d), 1.96 (3H, s), 2.49-2.52 (1H, m), 2.78-2.86 (1H, m), 3.47-3.53 (2H, m), 3.76 (1H, d), 4.01 (1H, d), 5.05-5.07 (1H, m), 5.62 (1H, br s), 6.57 (2H, d), 7.22 (2H, d), 7.45 (2H, s). |
| 7 | 1H-NMR (CDCl3) δ: 1.13-1.15 (3H, m), 1.47 (3H, d), 2.14-2.22 (2H, m), 2.49-2.51 (1H, m), 2.79-2.83 (1H, m), 3.46-3.52 (2H, m), 3.76 (1H, d), 4.01 (1H, d), 5.06-5.08 (1H, m), 5.61 (1H, d), 6.57 (2H, d), 7.24 (2H, d), 7.46 (2H, s). |
| 7-a | 1H-NMR (CDCl3) δ: 1.12-1.18 (3H, m), 1.48 (3H, d), 2.14-2.22 (2H, m), 2.51-2.53 (1H, m), 2.77-2.86 (1H, m), 3.47-3.53 (2H, m), 3.76 (1H, d), 4.01 (1H, d), 5.06-5.08 (1H, m) 5.56 (1H, d), 6.57 (2H, d), 7.27 (2H, d), 7.46 (2H, s). |
| 7-b | 1H-NMR (CDCl3) δ: 1.15 (3H, t), 1.47 (3H, d), 2.14-2.22 (2H, m), 2.48-2.53 (1H, m), 2.79-2.81 (1H, m), 3.47-3.52 (2H, m), 3.76 (1H, d), 4.01 (1H, d), 5.06-5.08 (1H, m), 5.60 (1H, d), 6.58 (2H, d), 7.24 (2H, d), 7.45 (2H, s). |
| 8 | 1H-NMR (CDCl3) δ: 0.66-0.73 (2H, m), 0.94-0.96 (2H, m), 1.25-1.30 (1H, m), 1.47 (3H, d), 2.48-2.52 (1H, m), 2.78-2.81 (1H, m), 3.47-3.53 (2H, m), 3.76 (1H, d), 4.01 (1H, d), 5.06-5.08 (1H, m), 5.80 (1H, br s), 6.58 (2H, d), 7.24 (2H, d), 7.45 (2H, s). |
| 8-b | 1H-NMR (CDCl3) δ: 0.66-0.76 (2H, m), 0.92-0.99 (2H, m), 1.23-1.36 (1H, m), 1.47 (3H, d), 2.49-2.51 (1H, m), 2.79-2.83 (1H, m), 3.47-3.53 (2H, m), 3.76 (1H, d), 4.01 (1H, d), 5.06-5.09 (1H, m), 5.78 (1H, d), 6.58 (2H, d), 7.22 (2H, d), 7.45 (2H, s). |
| 9 | 1H-NMR (CDCl3) δ: 1.48 (3H, d), 1.96 (3H, s), 2.60-2.62 (1H, m), 2.92-3.00 (1H, m), 3.49-3.60 (2H, m), 3.83 (1H, d), 4.15 (1H, d), 5.06-5.08 (1H, m), 5.60 (1H, d), 6.61 (2H, d), 7.25 (2H, d), 7.83 (2H, s), 7.91 (1H, s). |
| 9-b | 1H-NMR (CDCl3) δ: 1.47 (3H, d), 1.96 (3H, s), 2.60-2.62 (1H, m), 2.92-3.00 (1H, m), 3.50-3.60 (2H, m), 3.85 (1H, d), 4.15 (1H, d), 5.05-5.08 (1H, m), 5.61 (1H, br s), 6.61 (2H, d), 7.22 (2H, d), 7.86 (2H, s), 7.91 (1H, s). |
| 10 | 1H-NMR (CDCl3) δ: 1.14 (3H, t), 1.47 (3H, d), 2.14-2.22 (2H, m), 2.57-2.63 (1H, m), 2.92-2.99 (1H, m), 3.51-3.58 (2H, m), 3.83 (1H, d), 4.15 (1H, d), 5.06-5.08 (1H, m), 5.59 (1H, d), 6.61 (2H, d), 7.24 (2H, d), 7.85 (2H, s), 7.91 (1H, s). |
| 10-a | 1H-NMR (CDCl3) δ: 1.14 (3H, t), 1.48 (3H, d), 2.14-2.22 (2H, m), 2.60-2.62 (1H, m), 2.92-3.00 (1H, m), 3.51-3.58 (2H, m), 3.83 (1H, d), 4.15 (1H, d), 5.07-5.09 (1H, m), 5.55 (1H, d), 6.61 (2H, d), 7.24 (2H, d), 7.85 (2H, s), 7.91 (1H, s). |
| 10-b | 1H-NMR (CDCl3) δ: 1.15 (3H, t), 1.48 (3H, d), 2.17-2.19 (2H, m), 2.58-2.61 (1H, m), 2.92-3.00 (1H, m), 3.51-3.58 (2H, m), 3.83 (1H, d), 4.15 (1H, d), 5.07-5.09 (1H, m), 5.56 (1H, d), 6.61 (2H, d), 7.25 (2H, d), 7.85 (2H, s), 7.91 (1H, s). |
| 11 | 1H-NMR (CDCl3) δ: 0.66-0.76 (2H, m), 0.94-0.98 (2H, m), 1.23-1.32 (1H, m), 1.48 (3H, d), 2.57-2.65 (1H, m), 2.92-3.00 (1H, m), 3.51-3.58 (2H, m), 3.83 (1H, d), 4.13 (1H, d), 5.07-5.09 (1H, m), 5.83 (1H, br s), 6.61 (2H, d), 7.26 (2H, d), 7.85 (2H, s), 7.91 (1H, s). |
| 11-b | 1H-NMR (CDCl3) δ: 0.67-0.76 (2H, m), 0.92-1.00 (2H, m), 1.25-1.31 (1H, m), 1.49 (3H, d), 2.57-2.65 (1H, m), 2.92-3.00 (1H, m), 3.50-3.60 (2H, m), 3.83 (1H, d), 4.11 (1H, d), 5.07-5.09 (1H, m), 5.76 (1H, d), 6.61 (2H, d), 7.29 (2H, d), 7.85 (2H, s), 7.91 (1H, s). |
| 12 | 1H-NMR (CDCl3) δ: 0.16-0.22 (2H, m), 0.56-0.62 (2H, m), 0.91-0.99 (1H, m), 1.48 (3H, d), 2.14-2.16 (2H, m), 2.49-2.52 (1H, m), 2.78-2.81 (1H, m), 3.45-3.55 (2H, m), 3.76 (1H, d), 4.01 (1H, d), 5.08-5.14 (1H, m), 6.00 (1H, d), 6.58 (2H, d), 7.22 (2H, d), 7.45 (3H, s). |

TABLE 3-continued

| Compound No. | NMR |
|---|---|
| 12-b | 1H-NMR (CDCl3) δ: 0.17-0.19 (2H, m), 0.57-0.60 (2H, m), 0.93-0.97 (1H, m), 1.49 (3H, d), 2.14-2.16 (2H, m), 2.50-2.52 (1H, m), 2.80-2.81 (1H, m), 3.49-3.52 (2H, m), 3.76 (1H, d), 4.01 (1H, d), 5.09-5.11 (1H, m), 6.00 (1H, d), 6.58 (2H, d), 7.24 (2H, d), 7.43 (2H, s) |
| 13 | 1H-NMR (CDCl3) δ: 0.17-0.19 (2H, m), 0.58-0.60 (2H, m), 0.94-0.96 (1H, m), 1.49 (3H, d), 2.14-2.16 (2H, m), 2.58-2.62 (1H, m), 2.92-3.00 (1H, m), 3.52-3.59 (1H, m), 3.83 (1H, d), 4.15 (1H, d), 5.10-5.12 (1H, m), 6.00 (1H), 6.61 (2H, d), 7.25 (2H, d), 7.85 (2H, s), 7.91 (1H, s). |
| 13-b | 1H-NMR (CDCl3) δ: 0.17-0.19 (2H, m), 0.56-0.62 (2H, m), 0.91-0.98 (1H, m), 1.50 (3H, d), 2.13-2.18 (2H, m), 2.59-2.62 (1H, m), 2.92-2.99 (1H, m), 3.50-3.61 (2H, m), 3.83 (1H, d), 4.15 (1H, d), 5.09-5.12 (1H, m), 6.01 (1H, d), 6.61 (2H, d), 7.25 (2H, d), 7.85 (2H, s), 7.91 (1H, s). |
| 14 | 1H-NMR (CDCl3) δ: 1.44-1.49 (3H, m), 2.42-2.55 (3H, m), 2.77-2.86 (1H, m), 3.36 (3H, s), 3.45-3.67 (4H, m), 3.76 (1H, d), 4.01 (1H, d), 5.05-5.08 (1H, m), 6.32 (1H, d), 6.57 (2H, d), 7.21 (2H, d), 7.43 (2H, s). |
| 14-b | 1H-NMR (CDCl3) δ: 1.44-1.49 (3H, m), 2.44-2.50 (3H, m), 2.78-2.80 (1H, m), 3.36 (3H, s), 3.45-3.67 (4H, m), 3.76 (1H, d), 4.01 (1H, d), 5.05-5.08 (1H, m), 6.32 (1H, d), 6.57 (2H, d), 7.21 (2H, d), 7.44 (2H, s). |
| 15-b | 1H-NMR (CDCl3) δ: 1.44-1.47 (3H, m), 2.36-2.42 (3H, m), 2.60-2.65 (1H, m), 3.36 (3H, s), 3.50-3.69 (4H, m), 3.85 (1H, d), 4.15 (1H, d), 5.02-5.11 (1H, m), 6.34 (1H, d), 6.60 (2H, d), 7.22 (2H, d), 7.84 (3H, d). |
| 16-b | 1H-NMR (CDCl3) δ: 1.57-1.59 (3H, m), 2.58-2.62 (1H, m), 2.94-2.97 (1H, m), 3.50-3.61 (2H, m), 3.83 (1H, d), 4.16 (1H, d), 5.26-5.28 (1H, m), 6.04 (1H, d), 6.61-6.72 (4H, m), 7.29 (2H, d), 7.84 (2H, s), 7.91 (1H, s). |
| 17-b | 1H-NMR (CDCl3) δ: 0.64-0.77 (2H, m), 0.86-1.01 (2H, m), 1.25-1.31 (1H, m), 1.48 (3H, d), 2.53-2.63 (1H, m), 2.91-3.00 (1H, m), 3.48-3.62 (2H, m), 3.85 (1H, d), 4.11 (1H, d), 5.03-5.13 (1H, m), 5.80 (1H, d), 6.62 (2H, d), 7.27 (2H, d), 7.90 (2H, s). |

Biological Tests:

Unless not mentioned otherwise, the test solutions were prepared as follows:

Solvent: dimethyl formamide, 3 parts by weight

Emulsifier: polyoxyethylene alkyl phenyl ether, 1 part by weight

To prepare the test solution, 1 part by weight of an active compound is mixed with the above-mentioned amount of solvent containing the above-mentioned amount of emulsifier, and the mixture is diluted with water to the desired concentration.

R.H. means relative humidity; hrs means hours.

BIOLOGICAL TEST EXAMPLE 1.1

Tobacco Cutworm (*Spodoptera litura*) Larvae

Leaves of sweet potato were immersed in the test solution at the appropriate concentration, and the leaves were dried in air. The leaves were then placed in a petri dish having a diameter of 9 cm, and ten *Spodoptera litura* at third instar larvae were released therein. The petri dishes were placed in a temperature-controlled chamber at 25° C. After 2 days and 4 days more sweet potato leaves were added. After 7 days, the number of dead larvae was counted to calculate the insecticidal activity. An insecticidal activity of 100% means that all larvae were killed, whereas an insecticidal activity of 0% means that no larva was killed. In the current test, the results of two petri dishes for each treatment were averaged.

In this test the following compounds showed an insecticidal activity of 100% at an active compound concentration of 20 ppm: 1, 1-b, 2, 2-b, 3, 3-b, 4, 4-b, 5, 5-b, 6, 6-b, 7, 7-b, 8, 8-b, 9, 9-b, 10, 10-b, 11, 11-b. Compound No. 11-b showed an insecticidal activity of 100% at a concentration of 0.8 ppm.

In comparison, the compound No. 3-66 disclosed in WO2008/128711 having the following formula

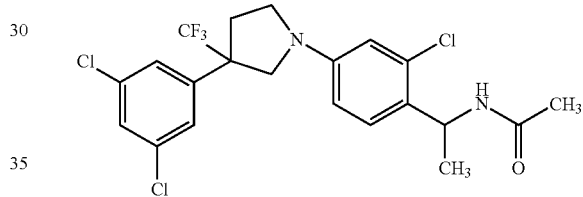

showed an insecticidal activity of just 20% at a concentration of 20 ppm.

BIOLOGICAL TEST EXAMPLE 1.2

Tobacco Cutworm (*Spodoptera litura*) Larvae Using Artificial Diet 2.3 g of artificial diet powder is put into a PET cup (7.5 cm diameter, 4 cm depth). The powder was leveled to make a layer in the bottom of the cup. 5 ml of a chemical solution is poured onto the powder and spread uniformly. The cup with treated diet powder is placed quiet to let the diet jell. Into each testing cup five 3rd-instar larvae were released. The testing cup is closed with the lid and placed in a temperature-controlled room at 25° C. and 50-60% R.H., 16L8D lighting conditions.

The mortality in % was determined according to the following criteria:
1 larva dead: 20% Efficacy
5 larvae dead: 100% Efficacy The following compounds showed an insecticidal activity of 100% at an active compound concentration of 20 ppm: 1, 1-b, 2, 2-b, 3, 3-b, 4, 4-b, 5, 5-b, 6, 6-b, 7, 7-b, 8, 8-b, 9, 9-b, 10, 10-b, 11, 12, 12-b, 13, 13-b, 14, 14-b, 15-b, 16-b, 17-b.

BIOLOGICAL TEST EXAMPLE 2

Two-Spotted Spider Mite *Tetranychus urticae*

50 to 100 adult mites of *Tetranychus urticae* were inoculated to leaves of kidney bean at two-leaf stage planted in a pot of 6 cm in diameter. After one day, test solution at the appropriate concentration was sprayed thereon in a sufficient amount using a spray gun. After the spraying, the plant pot was placed inside a greenhouse, and after 7 days, the acaricidal activity was calculated. An acaricidal activity of 100% means that all mites were killed, an acaricidal activity of 0% means that no mite was killed.

The following compounds showed an insecticidal activity of 100% at an active compound concentration of 100 ppm: 1-b, 2.

The following compounds showed an insecticidal activity of 100% at an active compound concentration of 20 ppm: 3, 3-b, 4, 4-b, 5, 5-b, 6, 6-b, 7, 7-b, 8, 8-b, 10, 10-b, 11, 11-b, 12, 12-b, 13, 13-b, 14, 14-b, 15-b, 16-b, 17-b. The compound No. 11-b showed an insecticidal activity of 100% at an active compound concentration of 4 ppm.

BIOLOGICAL TEST EXAMPLE 3

Cucurbit Leaf Beetle (*Aulacophora femoralis*)

Leaves of cucumber were immersed in the test solution at the appropriate concentration, and the leaves were dried in air. The leaves were then put in a plastic cup containing sterilized black soil and five *Aulacophora femoralis* at second instar larvae were released in the cup. The cups were placed in a temperature-controlled chamber at 25° C. After 7 days, the number of dead larvae was counted, and thus the insecticidal activity was calculated. An insecticidal activity of 100% means that all larvae were killed, whereas an insecticidal activity of 0% means that no larva was killed.

The following compounds showed an insecticidal activity of 100% at an active compound concentration of 100 ppm: 1, 7, 7-a, 12-b, 13-b, 14, 14-b, 15-b.

The following compounds showed an insecticidal activity of 100% at an active compound concentration of 20 ppm: 1-b, 2, 2-b, 3, 3-b, 4, 4-b, 5, 5-b, 7-b, 8, 8-b, 9-b, 10, 10-a, 10-b, 11, 11-b, 16-b, 17-b. The compound No. 11-b showed an insecticidal activity of 100% at an active compound concentration of 4 ppm.

In comparison, the compound No. 3-66 disclosed in WO2008/128711 having the following formula

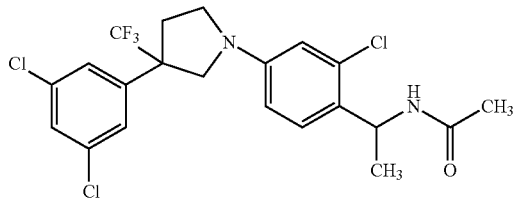 [SMILES: CC(=O)NC(C)c1ccc(N2CCC(c3cc(Cl)cc(Cl)c3)(C(F)(F)F)C2)cc1Cl]

showed an insecticidal activity of just 50% at a concentration of 20 ppm.

BIOLOGICAL TEST EXAMPLE 4

*Amblyomma hebraeum*—Test (AMBYHE)

Solvent: Dimethyl Sulfoxide

To produce a suitable preparation of active compound, 10 mg of active compound are dissolved in 0.5 ml solvent, and the concentrate is diluted with water to the desired concentration. Nymphs of the tick *Amblyomma hebraeum* are placed in perforated plastic beakers and immersed in aqueous compound solution for one minute. Ticks are transferred to a filter paper in a petridish and incubated in a climate chamber for 42 days.

After 42 days mortality in % is determined. 100% means that all the ticks have been killed; 0% means that none of the ticks have been killed.

In this test for example, the following compounds from the preparation examples showed good activity of 100% at application rate of 100 ppm: 2, 4, 5, 7, 8, 11, 2-b, 3-b, 4-b, 6-b, 7-b, 8-b, 10-b.

BIOLOGICAL TEST EXAMPLE 5

*Boophilus microplus* (Dip)

Solvent: Dimethyl Sulfoxide

To produce a suitable preparation of active compound, 10 mg of active compound are dissolved in 0.5 ml solvent, and the concentrate is diluted with water to the desired concentration. Eight to ten adult engorged female *Boophilus microplus* ticks are placed in perforated plastic beakers and immersed in aqueous compound solution for one minute. Ticks are transferred to a filter paper in a plastic tray. Egg deposition of fertile eggs is monitored after. After 7 days mortality in % is determined. 100% means that all the ticks have been killed; 0% means that none of the ticks have been killed.

In this test for example, the following compounds from the preparation examples showed good activity of 80% at application rate of 100 ppm: 15-b.

In this test for example, the following compounds from the preparation examples showed good activity of 100% at application rate of 100 ppm: 2, 3, 4, 5, 6, 7, 8, 11, 12, 14, 7-a, 1-b, 2-b, 3-b, 4-b, 5-b, 6-b, 7-b, 8-b, 10-b, 11-b, 14-b.

BIOLOGICAL TEST EXAMPLE 6

*Boophilus microplus*—Test (Injection)

Solvent: Dimethyl Sulfoxide

To produce a suitable preparation of active compound, 10 mg of active compound are dissolved in 0.5 ml solvent, and the concentrate is diluted with solvent to the desired concentration. Five adult engorged female ticks (*Boophilus microplus*) are injected with 1 µl compound solution into the abdomen. Ticks are transferred into replica plates and incubated in a climate chamber for a period of time. Egg deposition of fertile eggs is monitored.

After 7 days mortality in % is determined. 100% means that all eggs are infertile; 0% means that all eggs are fertile.

In this test for example, the following compounds from the preparation examples showed good activity of 100% at application rate of 20 µg/animal: 1, 2, 3, 4, 5, 6, 7, 8, 9, 10, 11, 12, 13, 14, 7-a, 10-a, 1-b, 2-b, 3-b, 4-b, 5-b, 6-b, 7-b, 8-b, 9-b, 10-b, 11-b, 14-b, 15-b.

BIOLOGICAL TEST EXAMPLE 7

*Ctenocephalides felis*—Test (CTECFE)

Solvent: Dimethyl Sulfoxide

To produce a suitable preparation of active compound, 10 mg of active compound are dissolved in 0.5 ml solvent, and the concentrate is diluted with cattle blood to the desired concentration. Approximately 20 adult unfed (*Ctenocephalides felis*) are placed in flea chambers. The blood chamber, sealed with parafilm on the bottom, are filled with cattle blood supplied with compound solution and placed on top of the flea chamber, so that the fleas are able to suck the blood. The blood chamber is heated to 37° C. whereas the flea chamber is kept at room temperature.

After 2 days mortality in % is determined. 100% means that all the fleas have been killed; 0% means that none of the fleas have been killed.

In this test for example, the following compounds from the preparation examples showed good activity of 80% at application rate of 100 ppm: 7-a.

In this test for example, the following compounds from the preparation examples showed good activity of 90% at application rate of 100 ppm: 14, 10-a.

In this test for example, the following compounds from the preparation examples showed good activity of 95% at application rate of 100 ppm: 2, 12, 8-b.

In this test for example, the following compounds from the preparation examples showed good activity of 100% at application rate of 100 ppm: 1, 3, 4, 5, 6, 7, 8, 9, 10, 11, 13, 1-b, 2-b, 3-b, 4-b, 5-b, 6-b, 7-b, 9-b, 10-b, 11-b, 14-b, 15-b.

BIOLOGICAL TEST EXAMPLE 8

*Lucilia cuprina* (48 Hrs)

Species: *Lucilia cuprina* $1^{st}$ Instar Larvae (Age 24 Hrs)
Solvent: Dimethyl Sulfoxide 10 mg active compound are dissolved in 0.5 ml dimethyl sulfoxide. Serial dilutions are made to obtain the desired rates. Approximately 20 *Lucilia cuprina* $1^{st}$ instar larvae are transferred into a test tube containing 1 $cm^3$ of minced horse meat and 0.5 ml aqueous dilution of test compound.

After 2 days larval mortality in % is recorded. 100% efficacy=all larvae are killed, % efficacy=normally developed larvae after 48 hrs.

In this test for example, the following compounds from the preparation examples showed good activity of 100% at application rate of 100 ppm: 1, 2, 3, 4, 5, 6, 7, 8, 9, 10, 11, 12, 13, 14, 7-a, 10-a, 1-b, 2-b, 3-b, 4-b, 5-b, 6-b, 7-b, 8-b, 9-b, 10-b, 11-b, 14-b, 15-b.

BIOLOGICAL TEST EXAMPLE 9

*Musca domestica*—Test

Solvent: Dimethyl Sulfoxide

To produce a suitable preparation of active compound, 10 mg of active compound are dissolved in 0.5 ml solvent, and the concentrate is diluted with water to the desired concentration. Prior to the assay, a piece of kitchen sponge is soaked with a mixture of sugar and compound solution and placed into a container. 10 adults (*Musca domestica*) are placed into the container and closed with a perforated lid.

After 2 days mortality in % is determined. 100% means that all the flies have been killed; 0% means that none of the flies have been killed.

In this test for example, the following compounds from the preparation examples showed good activity of 80% at application rate of 100 ppm: 2, 5, 7, 1-b, 2-b, 5-b, 6-b, 14-b.

In this test for example, the following compounds from the preparation examples showed good activity of 90% at application rate of 100 ppm: 3, 8, 10, 9-b.

In this test for example, the following compounds from the preparation examples showed good activity of 100% at application rate of 100 ppm: 4, 9, 11, 3-b, 4-b, 7-b, 8-b, 10-b, 11-b.

PREPARATION EXAMPLE 1

Granules

To a mixture containing 10 parts of the compound of the present invention (e.g. compound No. 1), 30 parts of bentonite (montmorillonite), 58 parts of talc and 2 parts of lignin sulfonate was added 25 parts of water, and the mixture was well kneaded and granulated with 10 to 40 meshes by an extruding granulator and dried at 40 to 50° C. to obtain granules.

PREPARATION EXAMPLE 2

Granules 95 parts of clay mineral granules having particle diameter distribution within the range of 0.2 to 2 mm were put into a rotary mixer, and then wetted evenly by spraying of 5 parts of the compound of the present invention (e.g. compound No. 1) together with a liquid diluent under rotating condition and dried at 40 to 50° C. to obtain granules.

PREPARATION EXAMPLE 3

Emulsion 30 parts of the compound of the present invention (e.g. compound No. 1), 55 parts of xylene, 8 parts of polyoxyethylene alkyl phenyl ether and 7 parts of calcium alkylbenzenesulfonate were mixed together to obtain the emulsion.

PREPARATION EXAMPLE 4

Wettable Agent 15 parts of a compound according to the invention (e.g. compound No. 1), 80 parts of a mixture of white carbon (hydrated amorphous silicon oxide fine powder) and powdered clay (1:5), formalin condensate of 2 parts of sodium alkylbenzenesulfonate and 3 parts of sodium alkylnaphthalenesulfonate were mixed together and the mixture was crushed to obtain a wettable agent.

PREPARATION EXAMPLE 5

Wettable Granules 20 parts of a compound according to the invention (e.g. compound no. 1), 30 parts of lignin sodium sulfonate, 15 parts of bentonite and 35 parts of calcined diatomaceous earth powder were well mixed, and after addition of water, the mixture was then extruded with a screen of 0.3 mm and dried to obtain wettable granules.

The invention claimed is:
1. Arylpyrrolidine compounds of formula (I)

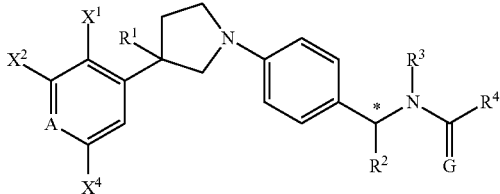

wherein
A is C—X³ or nitrogen;
X¹, X², X³ and X⁴ are each independently hydrogen, halogen, $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl;
R¹ is $C_{1-4}$ haloalkyl;
R² is $C_{1-4}$ alkyl, $C_{1-4}$ haloalkyl, $C_{3-6}$ cycloalkyl or cyano;
R³ is hydrogen, $C_{1-4}$ alkyl or $C_{1-4}$ haloalkyl;
R⁴ is $C_{1-4}$ alkyl, $C_{1-4}$ haloalkyl, $C_{3-6}$ cycloalkyl, $C_{3-6}$ cycloalkyl-$C_{1-4}$ alkyl; $C_{3-6}$ halocycloalkyl, $C_{1-4}$ alkoxy, $C_{1-4}$ alkoxy-$C_{1-4}$ alkyl, $C_{1-4}$ haloalkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, $C_{1-4}$ haloalkylthio-$C_{1-4}$ alkyl, $C_{1-4}$ haloalkylsulfinyl-$C_{1-4}$ alkyl, $C_{1-4}$ haloalkylsulfonyl-$C_{1-4}$ alkyl, $C_{1-4}$ alkylamino, or halogen substituted phenyl; and
G is O or S.

2. The arylpyrrolidine compounds according to claim 1, wherein
A is C—X³;
X¹, X², X³ and X⁴ are each independently hydrogen, halogen, or $C_{1-4}$ haloalkyl;
R¹ is trifluoromethyl;
R² is methyl, ethyl or cyclopropyl;
R³ is hydrogen;
R⁴ is methyl, ethyl, cyclopropyl, cyclopropylmethyl, 2,2,2-trifluoroethyl, 2-methoxyethyl, methylthiomethyl, methylsulfinylmethyl, methylsulfonylmethyl or 2,4,6-trifluorophenyl; and
G is O.

3. The arylpyrrolidine compounds according to claim 1, wherein
A is C—H, C—Cl or CCF₃;
X¹, X², X³ and X⁴ are each independently hydrogen, fluorine, chlorine, bromine or CF₃;
R¹ is trifluoromethyl;
R² is methyl;
R³ is hydrogen;
R⁴ is methyl, ethyl, cyclopropyl, cyclopropylmethyl, methoxyethyl, or 2,4,6-trifluorophenyl; and
G is O.

4. The arylpyrrolidine compounds according to claim 1, wherein
A is C—X³;
X¹, X², X³ and X⁴ are each independently hydrogen, chlorine or CF₃;
R¹ is trifluoromethyl;
R² is methyl;
R³ is hydrogen;
R⁴ is methyl, ethyl, cyclopropyl, cyclopropylmethyl, methoxyethyl, or 2,4,6-trifluorophenyl; and
G is O.

5. The arylpyrrolidine compounds according to claim 1, wherein
A is C—X³;
X¹, X³, and R³ each is hydrogen;
X², X⁴, and R¹ each is CF₃;
R² is methyl;
R⁴ is methyl, ethyl, cyclopropyl, cyclopropylmethyl, methoxyethyl, or 2,4,6-trifluorophenyl; and
G is O.

6. The arylpyrrolidine compounds according to claim 1, wherein
A is C—X³;
X¹, X³, and R³ each is hydrogen;
X², and X⁴ each is chlorine;
R¹ is CF₃;
R² is methyl;
R⁴ is methyl, ethyl or cyclopropyl; and
G is O.

7. The arylpyrrolidine compounds according to claim 1, wherein
A is C—X³;
X¹, X³, R³ each is hydrogen;
X² is chlorine;
R¹, X⁴ each is CF₃;
R² is methyl;
R⁴ is methyl, ethyl or cyclopropyl; and
G is O.

8. The arylpyrrolidine compounds according to claim 1, wherein
A is C—X³;
X¹, R³ each is hydrogen;
X², X³, X⁴ each is chlorine;
R¹ is CF₃;
R² is methyl;
R⁴ is methyl, ethyl, cyclopropyl, cyclopropylmethyl, or methoxyethyl; and
G is O.

9. The arylpyrrolidine compounds according to claim 1, wherein
A is nitrogen;
X¹, X³ each is hydrogen;
X², X⁴, R¹ each is CF₃;
R² is methyl;
R⁴ is cyclopropyl; and
G is O.

10. A pesticidal composition comprising at least one arylpyrrolidine compound according to claim 1 for controlling insects, arachnids, helminths, nematodes, and molluscs.

11. The pesticidal composition according to claim 10, which additionally comprises at least another active ingredient selected from the group consisting of insecticides, acaricides, nematicides, fungicides, biological control agents and bacterizides.

12. A pharmaceutical composition comprising at least one arylpyrrolidine compound according to claim 1 for controlling endoparasites or ectoparasites.

13. A method for the preparation of arylpyrrolidine compounds according to claim 1 comprising reacting a compound of formula (II)

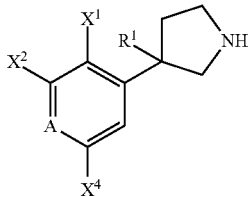
(II)

with a compound of formula (III)

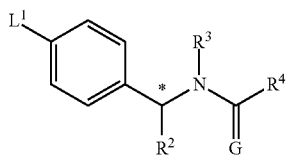
(III)

in a diluent, optionally in the presence of a base, and optionally in the presence of a catalyst, wherein in the formulae (II) and (III)

A is C—$X^3$ or nitrogen;
$X^1$, $X^2$, $X^3$ and $X^4$ are each independently hydrogen, halogen, $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl;
$R^1$ is $C_{1-4}$ haloalkyl;
$R^2$ is $C_{1-4}$ alkyl, $C_{1-4}$ haloalkyl, $C_{3-6}$ cycloalkyl or cyano;
$R^3$ is hydrogen, $C_{1-4}$ alkyl or $C_{1-4}$ haloalkyl;
$R^4$ is $C_{1-4}$ alkyl, $C_{1-4}$ haloalkyl, $C_{3-6}$ cycloalkyl, $C_{3-6}$ cycloalkyl-$C_{1-4}$ alkyl; $C_{3-6}$ halocycloalkyl, $C_{1-4}$ alkoxy, $C_{1-4}$ alkoxy-$C_{1-4}$ alkyl, $C_{1-4}$ haloalkoxy-$C_{1-4}$ alkyl, $C_{1-4}$ alkylthio-$C_{1-4}$ alkyl, $C_{1-4}$ alkylsulfinyl-$C_{1-4}$ alkyl, $C_{1-4}$ alkylsulfonyl-$C_{1-4}$ alkyl, $C_{1-4}$ haloalkylthio-$C_{1-4}$ alkyl, $C_{1-4}$ haloalkylsulfinyl-$C_{1-4}$ alkyl, $C_{1-4}$ haloalkylsulfonyl-$C_{1-4}$ alkyl, $C_{1-4}$ alkylamino, or halogen substituted phenyl;
G is O or S; and
$L^1$ is halogen or $C_{1-4}$ haloalkylsulfonyloxy.

14. A method for the preparation of compounds of formula (II) comprising (i) reacting a compound of formula (VI)

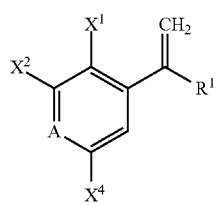
(VI)

with a substituted trimethylsilylmethyl($C_{1-6}$)alkylamine compound selected from the group consisting of N-benzyl-1-methoxy-N-[(trimethylsilyl)methyl]methanamine, N-benzyl-1-butoxy-N-[(trimethylsilyl)methyl]-methanamine and N-(butoxymethyl)-N-[(trimethylsilyl)methyl]cyclohexylamine in the presence of a catalyst to obtain an arylpyrrolidine compound of formula (VII)

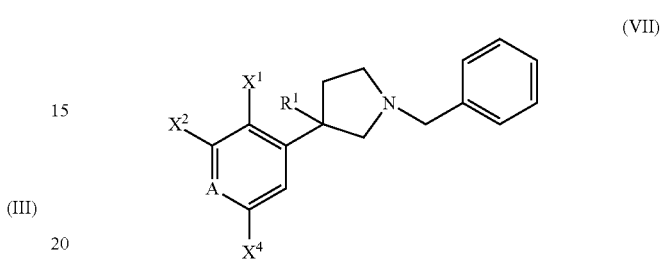
(VII)

and (ii) removing the benzyl group from the compound of formula (VII), wherein in the formulae (VI) and (VII)

A is C—$X^3$ or nitrogen;
$X^1$, $X^2$, $X^3$ and $X^4$ are each independently hydrogen, halogen, $C_{1-4}$ haloalkyl, $C_{1-4}$ haloalkoxy, $C_{1-4}$ haloalkylthio, $C_{1-4}$ haloalkylsulfinyl or $C_{1-4}$ haloalkylsulfonyl; and
$R^1$ is $C_{1-4}$ haloalkyl.

15. The arylpyrrolidine compounds according to claim 1 in the (S)-configuration as given in formula (I-b)

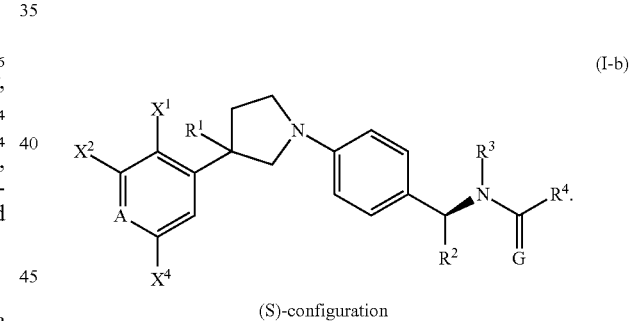
(I-b)

(S)-configuration

16. A pesticidal composition comprising at least one arylpyrrolidine compound according to claim 15 for controlling insects, arachnids, helminths, nematodes, and molluscs.

17. The pesticidal composition according to claim 16, further comprising at least another active ingredient selected from the group consisting of insecticides, acaricides, nematicides, fungicides, biological control agents and bacterizides.

18. A pharmaceutical composition comprising at least one arylpyrrolidine compound according to claim 15 for controlling endoparasites or ectoparasites.

* * * * *